(12) United States Patent
Douen

(10) Patent No.: US 8,863,031 B2
(45) Date of Patent: Oct. 14, 2014

(54) SYSTEMS, METHODS AND ARTICLES FOR MANAGING PRESENTATION OF INFORMATION

(76) Inventor: Andre Gene Douen, Mississauga (CA)

( * ) Notice: Subject to any disclaimer, the term of this patent is extended or adjusted under 35 U.S.C. 154(b) by 452 days.

(21) Appl. No.: 13/006,777

(22) Filed: Jan. 14, 2011

(65) Prior Publication Data

US 2011/0179389 A1    Jul. 21, 2011

Related U.S. Application Data

(63) Continuation-in-part of application No. 12/504,941, filed on Jul. 17, 2009.

(51) Int. Cl.
G09B 23/28 (2006.01)
G06F 19/00 (2011.01)

(52) U.S. Cl.
CPC .............. G09B 23/28 (2013.01); *G06F 19/34* (2013.01); *G06F 19/32* (2013.01)
USPC ........... 715/828; 715/705; 715/707; 715/742; 434/262

(58) Field of Classification Search
CPC .......... G06F 3/048; G06F 19/32; G06F 19/34
USPC .................... 434/262; 715/705, 707, 742, 828
See application file for complete search history.

(56) References Cited

U.S. PATENT DOCUMENTS

| | | | |
|---|---|---|---|
| 7,050,753 B2 | 5/2006 | Knutson | |
| 7,085,800 B2 | 8/2006 | Abbott et al. | |
| 7,360,158 B1 | 4/2008 | Beeman | |
| 7,374,535 B2 | 5/2008 | Schoenberg et al. | |
| 7,412,511 B2* | 8/2008 | Curry | 709/225 |
| 7,437,684 B2 | 10/2008 | Maille et al. | |

(Continued)

FOREIGN PATENT DOCUMENTS

WO    WO-2004061743 A2    7/2004

OTHER PUBLICATIONS

"A.D.A.M. Interactive Anatomy 4 Student Edition" Software, 2006, Web page www.adam.com/Our_Products/School_and_Instruction/Students/Higher_Education/aia.html and www.adam.com/aia/features.htm, snapsjots of Jun. 23, 2007-Jul. 14, 2007 downloaded from www.archieve.org using the Wayback machine, p. 1-17, and User Manual, p. 1-28.*

(Continued)

Primary Examiner — Amy Ng
Assistant Examiner — Claudia Dragoescu
(74) Attorney, Agent, or Firm — Hunter Clark PLLC

(57) ABSTRACT

Disclosed are methods, systems, and articles, such as computer program products, including a method for managing presentation of information, performed by execution of computer readable program code by a processor of a computer system, is disclosed. The method includes retrieving information relating to one or more subject matters from one or more data repositories, the one or more subject matters including general non-personal information on medical conditions and treatments therefor, presenting one or more sets of data from the retrieved information specific to a practitioner type selectable by a user from a plurality of practitioner types, presenting another one or more sets of data from the retrieved information common to two or more practitioner types selectable from the plurality of practitioner types, and presenting a further one or more sets of data from the retrieved information specific to at least one non-practitioner type.

20 Claims, 21 Drawing Sheets

(56) References Cited

U.S. PATENT DOCUMENTS

| | | |
|---|---|---|
| 7,454,386 B2 | 11/2008 | Chakraborty |
| 7,487,453 B2 | 2/2009 | Goebel et al. |
| 7,502,770 B2 | 3/2009 | Hillis et al. |
| 7,517,220 B2 | 4/2009 | Corn et al. |
| 7,862,340 B2 | 1/2011 | Chen et al. |
| 8,132,101 B2 | 3/2012 | Buck et al. |
| 2002/0087416 A1 | 7/2002 | Knutson |
| 2003/0107591 A1 | 6/2003 | Jameson |
| 2004/0078211 A1* | 4/2004 | Schramm-Apple et al. ...... 705/1 |
| 2004/0078215 A1 | 4/2004 | Dahlin et al. |
| 2004/0125126 A1 | 7/2004 | Egawa et al. |
| 2005/0039127 A1 | 2/2005 | Davis |
| 2005/0060205 A1 | 3/2005 | Woods et al. |
| 2005/0075544 A1 | 4/2005 | Shapiro et al. |
| 2005/0131738 A1 | 6/2005 | Morris |
| 2005/0228593 A1 | 10/2005 | Jones |
| 2006/0031094 A1 | 2/2006 | Cohen et al. |
| 2007/0048710 A1 | 3/2007 | Olson |
| 2007/0061393 A1 | 3/2007 | Moore |
| 2007/0122783 A1 | 5/2007 | Habashi |
| 2007/0136676 A1 | 6/2007 | Kruempelmann et al. |
| 2007/0220004 A1 | 9/2007 | Fifield et al. |
| 2007/0234219 A1 | 10/2007 | Bhattaru |
| 2008/0098333 A1 | 4/2008 | Champion et al. |
| 2008/0141130 A1 | 6/2008 | Moore et al. |
| 2008/0201174 A1* | 8/2008 | Ramasubramanian et al. .. 705/3 |
| 2009/0089709 A1 | 4/2009 | Baier et al. |
| 2009/0106051 A1 | 4/2009 | Albro et al. |
| 2009/0263777 A1 | 10/2009 | Kohn |
| 2011/0016427 A1 | 1/2011 | Douen |

OTHER PUBLICATIONS

"Biovere's Anatomica 3D: Musculoskeletal System", http://www.biovere.com/cart/a3d.php, Article, 2009.

Trademark: I.E. I.Nformation & E.Ducation Software & Design, Registered, 1013039, TMA549585, filed Apr. 26, 1999.

Trademark: The Good Food Game & Design, Registered, 0898727, TMA552455, filed Dec. 8, 1998.

Visible Body | 3D Human Anatomy | Rour: What Is It?, Argosy Publising, Inc., 2007-2009.http://www.visiblebody.com/Tour_What_Is_It. Article.

Written Opinion & International Search Report for PCT/CA/2010/001083 dated Nov. 4, 2010.

* cited by examiner

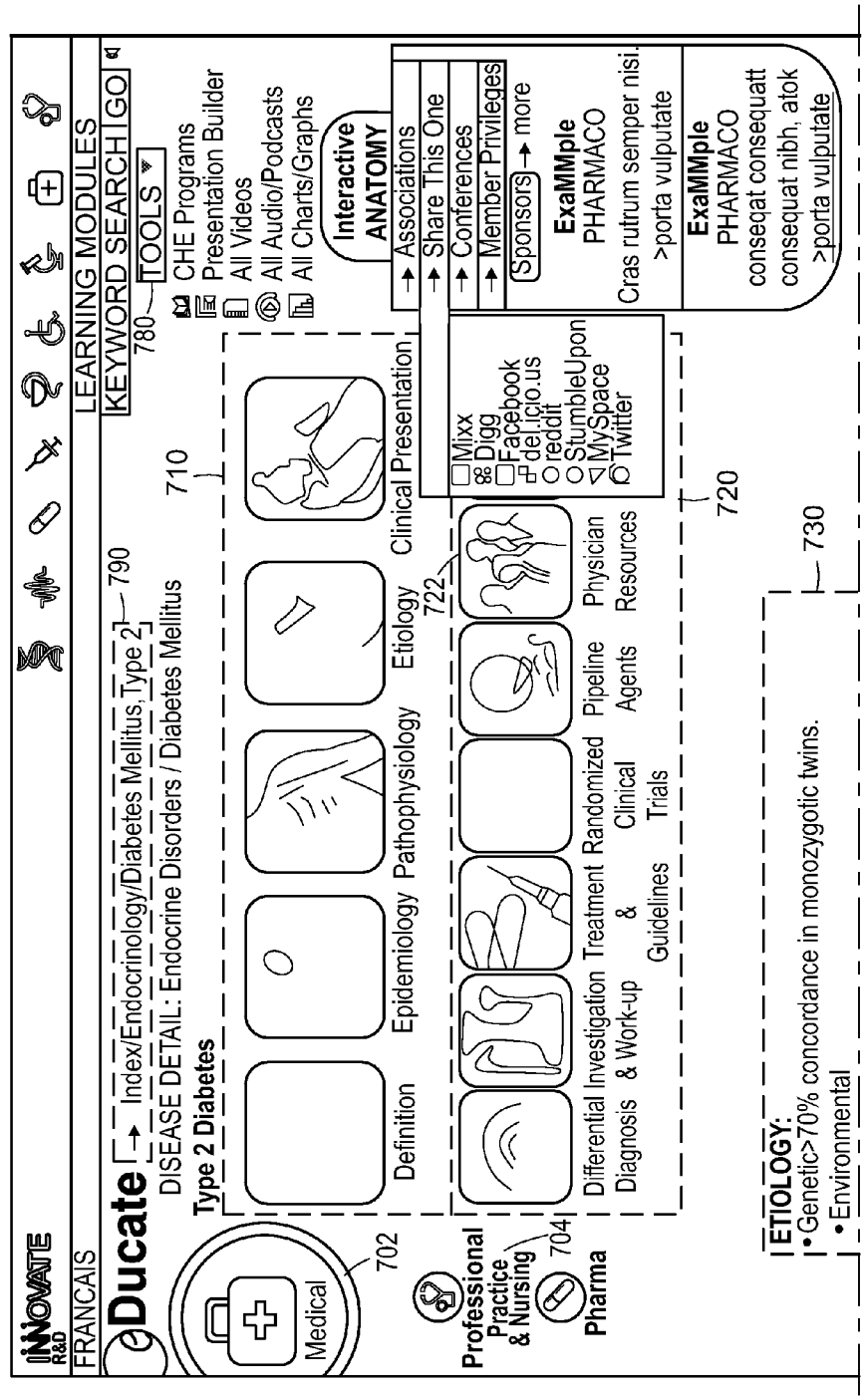

| CLUSTER HEADACHE |||||
|---|---|---|---|
| Idiopathic, unilateral, brief but severe headache that is specifically accompanied by autonomic symptoms |||||
| CLINICAL PRESENTATION | DIFFERENTIAL DIAGNOSIS | INVESTIGATIONS AND WORKUP | TREATMENT AND GUIDELINES |
| Includes:<br>Pain<br>• Severe unilateral temporal orbital or supraorbital<br>• Usually ocours regularly for few months followed by months to year symptom free intervals.<br>• Ipsilateral autonomic symtoms are usually present: eg.<br>  ∘ Ptosis, miosis, lacrimation, conjunctival injection, rhinorrhea, and nasal congestion<br>• Partial horner's syndrome may be seen | • Trigeminal neuralgia<br>• Primary stabbing headache<br>• Paroxysmal hemicrania<br>• Secondary headaches | • Diagnosed by clinical evaluation and Hx of headaches:<br>• Key questions:<br>Intrigue about the quality of pain (Deep excruciating, continuous pain lasting upto an hr reaching its peak intensity within few mins.)<br>Observe redness, ptosis of the eye of effected side<br>• CT scan or MRI is done to see any structural deformity | • Best intial therapy:<br>∘ 100% oxygen inhalation<br>∘ Sumatriptan SC 6mg/day<br>∘ Nasal spray 20mg.<br>• Prophylactic therapy: Verapamil P/O 120-160mg/daily TID. Alternates choices includes glucocorticoids, lithium and methylserguide |

"Patient Health Profile"

| Current as of : | Dec 25th, 20xx | |
|---|---|---|
| Patient ID : | Name or Initials _____ | |
| | Gender : M / F | Age: 78 |
| Medical History | Year Diagnosed | Medications |
| - Arthritis | 2006 | |
| - Diabetes<br>- T1 or T2 | 2002 | 1. Metformin 500mg twice daily |
| - Cholesterol | 2009 | 1. Crestor 5 mg daily |
| - Heart Disease | 2008 | 1. Aspirin 325 mg daily |
| - High Blood Pressure | | 1. HCTZ 25 mg daily<br>2. _____<br>3. _____ |
| - Stroke | 2009 | 1. Aspirin 325 mg daily |
| - Smoking | 1980 | Stopped June 2009 |
| | | |
| Laboratory : | | |
| Chest x-ray | 2009 | Normal |
| CT brain | 2009 | Showed the stroke – right brain |
| Blood glucose | Dec 2010 | 6.1 |
| | | |
| Clinical monitoring | | |
| BP | dec1 2010-12-12 | Morning - 160/90<br>Afternoon – 140/85 |
| | | |
| | | |

FIG. 18

SYSTEMS, METHODS AND ARTICLES FOR MANAGING PRESENTATION OF INFORMATION

CROSS-REFERENCE TO RELATED APPLICATIONS

This application is a continuation-in-part application of non-provisional U.S. patent application Ser. No. 12/504,941, entitled "SYSTEMS, METHODS AND ARTICLES FOR MANAGING PRESENTATION OF INFORMATION," and filed Jul. 17, 2009, the content of which is hereby incorporated by reference in its entirety.

BACKGROUND

The present disclosure relates to presentation of information, and more particularly to managing presentation of information on an interface used by multiple user types.

Conventional data repositories and interfaces to access and present data stored on such repositories are often cumbersome and not user friendly. Furthermore, conventional data repositories and interfaces for using them are generally not well adapted to facilitate e-learning for a wide range of different professionals within any given field or discipline. For example, with respect to medical e-learning systems, there is no single system currently available that simultaneously reaches a wide range of health care professionals such as physicians, pharmacists, nurses, advanced practice nurses, physician assistants, allied health workers, and students.

Additionally, many professional disciplines (health, law, etc.) require certification through professional examinations and/or continuing education programs, and thus require regular continuous access to current research and development in the respective areas of professional disciplines. For example, health care professionals have to keep apprised of current scientific and medical research, including numerous ongoing clinical trials that continually impact on health care practice. Consequently, a challenge exists for delivering information harvested from new scientific/medical research, including new clinical trial data, in a timely fashion to healthcare professionals. The challenge also includes conveying new drug/pharmaceutical information, including benefits, risks and adverse events associated with drugs/medications, to the health care community, as well as disseminating new information/data regarding risks and benefits of interventional procedures and devices.

Health care professionals also require access to publications providing recommendations for patient care, including interventional procedures and drug use are available in "Best Practice Guidelines" or "Current Clinical Guidelines." These publications include a composite outcome of past and new research data often generated from an expert panel and may or may not be supported by a Health Care Association. However, while the use of such guidelines is helpful, some short comings include: (i) they are often not universal and may be regional or specific to a particular country, (ii) they represent only the opinions of the members of the review panel, (iii) they are updated at variable time intervals often years apart, (iv) they are usually published in a journal specific to the disease or on an online site specific to the disease with limited readership and so the information/recommendations are often not widely distributed across the medical community and with even much less reach to other health care professionals, and (v) the information is often voluminous and typically distributed over multiple websites such that information retrieval is often tedious and requires multi-website search, i.e. there is no one website that effectively harvests this type of data.

Consequently, there is a major challenge in delivering to health care professionals (as well as delivering information to non-practitioners) current medical, nursing and pharmaceutical information in a practical format and within a timely fashion. Similar challenges exist in delivering current information in other disciplines, including law, engineering, natural sciences, social sciences, arts, etc.

SUMMARY

Embodiments of the present disclosure relate to systems including user interfaces configured to manage presentation of data. In some embodiments, the data whose presentation is to be managed includes medical data, including data pertaining to medical conditions and treatments therefore, data pertaining to health care education, including the presentation of continuing health education materials, etc. The systems and interfaces enable the presentation of some common portions of the data to several types of users, e.g., different types of health care practitioners including physicians, pharmacists, nurse practitioners, etc., and present other portions of such data to specific user types. For example, in situations where health professionals, e.g., a doctor, a nurse and/or a pharmacist, are to view data pertaining to a particular disease, an interface enables a doctor user-type to view certain data portions pertaining to that disease (for example, data relating to medical procedures that generally only doctors would be authorized to perform on patients), but will not present this information if other types of health care professionals are specified. Similarly, a pharmacist may be able to view specific data portions pertaining to the particular disease that a doctor and/or other types of health professional do not generally view, e.g., specific chemical structures/configurations of certain medications to treat a particular condition. On the other hand, two or more (or all) of the health professional types may be allowed to access and view certain common portions of data (e.g., background information relating to the disease).

In some variations, the presentation interface is configured as a "drill-down" interface such that a user can navigate the interface to present data the user is looking for by selecting progressively more specific user selectable items (e.g., icons, links, selections button, text fields, etc.) At least some of the content (e.g., particular screens or pages) presented in response to certain user selections may include some data unique to a specific user type, while some content (for example, on a particular presented screen/page) may be common to two or more user types.

In some implementations, the data presentation management system may include an interactive anatomical model that provides data (graphical data, text data, etc.) to the user upon selection of specific positions on the model. The model may be configured as a "peel-away" model such that certain graphical layers can be displayed or suppressed. The model may also be configured with "hover functionality" such that hovering the cursor over a specifically defined area on the model, such as over the heart, may trigger a list of medical conditions specific to the that organ from which the user can click and be transferred to further medical, nursing or pharmacy data depending the user type navigating the system. A lay public interactive model will display basic medical information on the topic, and may be used in the same format. In some embodiments, the data presentation management system includes a tools menu to activate certain tools/applications such as the preparation of presentations (e.g., Power- Point presentations) from data available to user via the interface, execution of continuing education presentations, etc.

The systems, methods and articles described herein enable, among other things: 1) promotion of education in general, 2) manage access to large volumes of data relating to one or more subject matters, including medical/nursing/pharmacologic/scientific data, 3) define an educational distribution channel that bridges related healthcare groups (physicians, nurses and pharmacists), 4) provide a comprehensive standardized review of existing knowledge within a field or discipline together with presentation of emerging therapies and "cutting edge" information, 5) provide an education platform standardized through use of clearly defined icons that relates to a specific educational content within a given field, 6) implement continuing health education (CHE) programs developed for promoting advancement in healthcare and patient care, 7) overcome barriers in continuing health education by providing a single repository (e.g., the eDucate platform) to access all medical, nursing, pharma CHE programs developed independently or in association with pharmaceutical companies, 8) provide continuous education updates presented in a summarized and succinct fashion on the background of core information within a given field, and 9) implement a platform to enable user-testing of learned educational material (e.g., administer quizzes and review exams).

In one aspect, a method, performed by execution of computer readable program code by a processor of a computer system, for managing presentation of information is disclosed. The method includes retrieving information relating to one or more subject matters from one or more data repositories, the one or more subject matters including general non-personal information on medical conditions and treatments therefor, presenting one or more sets of data from the retrieved information specific to a user type selected by a user from a plurality of user types, and presenting another one or more sets of data from the retrieved information common to two or more user types selected from the plurality of user types.

Embodiments of the method may include one or more of the following features.

Retrieving information relating to one or more subject matters may include retrieving information from the one or more data repositories implemented, at least in part, at one or more of, for example, one or more remote computer servers connected to the computer system via a network and/or one or more storage media locally connected to the computer system.

The computer system may include one or more handheld computing devices including one or more of, for example, an iPhone™, iPad, a Blackberry™, Android-based phone, and/or another smart phone device.

The one or more subject matters may include health care.

The plurality of user types may include one or more of, for example, a physician, a nurse, a pharmacists, a physician assistant, a doctor of osteopathy, a paramedic/emergency medical technician (EMS), a registered practical nurse, a nursing aide and/or a health care student.

Presenting the other one or more sets of data common to the two or more user types may include displaying on a display device a landing page identifying at least one of the two or more user types and the one or more subject matters. The landing page may include user selectable items respectively associated with the at least one of the two or more user types.

The method may further include displaying, in response to user selection of one of the user selectable items identifying the at least one of the two or more user types, a topics page including a listing of topics relating to the one or more subject matters. The listing of topics may include a listing of health care topics.

The topics page may further include a tools menu identifying one or more computer-implemented tools to perform one or more of, for example, accessing available data and/or processing the available data.

The one or more computer-implemented tools may include, for example, a Continuing Health Education tool implemented for a topic selected from the listing of topics presented in the topics page to present to the user educational materials relating to the selected topic, a Presentation Builder tool to construct a presentation based on one or more, for example, of an audio data and/or visual data to be provided to the user, an All Video tool to present videos relating to the topic selected from the listing of topics presented in the topics page, an Audio and Podcast tool to present audio data relating to the topic selected from the listing of topics presented in the topics page and/or a Charts and Graphs tool to present graphical information relating to the topic selected from the listing of topics presented in the topics page.

The Continuing Health Education tool implemented to present to the user the educational materials relating to selected topic may include a tool configured to present to the user one or more of, for example, an educational slide-show presentation and a video presentation relating to the selected topic.

The Continuing Health Education tool implemented to present to the user the educational materials relating to selected topic may include a tool configured to present to the user one or more exams adapted to assess knowledge of the user and facilitate learning of the one or more subject matters.

Displaying the topics page may include presenting, based on the selected user type, a model relevant to the one or more subject matters.

Presenting the model may include presenting an interactive anatomical model including graphical data relating to at least one topic selected from the listing of topics relating to health care presented in the topics page. The anatomical model may include a composite of graphical layers that are each representative of different anatomical structures of the human body, at least one of the graphical layers is configured to be interactively displayed or suppressed. The graphical layers include one or more of, for example, a skeletal layer representative of a skeleton of the human body, a muscle and tendons layer representative of the muscular and tendon anatomy of the human body, a vascular layer representative of the blood vessel anatomy of the human body, a skin layer representative of the dermatological layout of the human body, a fat and fascia layer, an organ layer representative of organs of the human body, a digestive tract layer representative of a digestive tract of the human body, a respiratory system layer representative of a respiratory system of the human body, a cardiovascular/vascular system representative of a cardiovascular/vascular system of the human body, a nervous system layer representative of a nervous system of the human body, an endocrine system layer representative of an endocrine system of the human body, a reproductive system layer representative of the reproductive system of the human body and/or a lymphatic layer representative of the lymphatic system of the human body.

Presenting the interactive anatomical model may include selecting one or more positions on the interactive anatomical model to cause medical data corresponding to the selected one or more positions to be displayed. Presenting the interactive anatomical model may include presenting anatomical user selectable items that include items representative of one or more of, for example, anatomy data corresponding to the selected one or more positions, physiology data corresponding to the selected one or more positions and/or pathology/pathophysiology data corresponding to the selected one or more positions.

Presenting the model may include presenting a molecular assimilation model including graphical data relating to at least one topic selected from the listing of topics relating to the one or more subject matters. The molecular assimilation model may include a composite-layer interactive graphical molecular model depicting the interaction of substances with one or more of cells in the human body and organs in the human body.

Displaying the topics page may include displaying, in a portion of the topics page, a list of one or more sponsors that includes associated links for at least one of the plurality of user types to access additional information relating to information provided on the topics page from data repositories of the some of the one or more sponsors.

The method may further include presenting, in response to selection of a topic from the listing of topics relating to health care, a disease selection page including a list of diseases associated with the selected topic.

The disease selection page may further include an interactive model to present data pertaining to the selected topic.

The method may further include presenting, in response to selection of a disease from the list of diseases associated with the selected topic, a disease detail page containing data specific to the selected disease. Presenting the disease detail page may include presenting a first area including user selectable items common to the two or more user types, presenting a second area including user selectable items specific to the selected user type, and presenting a third area including data relating to the selected disease retrieved in response to selection of one of the user selectable items from the first area or the second area.

The user selectable items common to the two or more user types may include a disease definition icon, an epidemiology icon, a pathophysiology icon, an etiology icon and/or a clinical presentation icon.

Presenting the third area may include providing links to access additional data related to the data presented in the third area, the additional data including one or more of, for example, text-based data, image data, video data and/or audio data.

Presenting the third area may include presenting data in the third area in one or more of, for example, a bullet format and/or a list format.

Presenting the second area may include presenting user selectable resource items specific to the selected user type, the user selectable resource items being associated with one or more computer-implemented tools. The selected user type may be a physician, and the associated one or more computer-implemented tools may include one or more of, for example, a differential diagnosis tool, an investigation and workup tool, a treatment and guidelines tool to provide data regarding treatments and guidelines for the selected disease, a randomize clinical trial tool, a pipeline agent associate with a tool to provide data on new and emerging therapies within a disease area, a physician resources tool and/or a references tool.

The method may further include presenting in response to selection of the resources tool list of tools including one or more of, for example, a disease management flow chart and/or decision making tools.

The selected user type may be a pharmacist, and the associated one or more computer-implemented tools may include one or more of, for example, a clinical outcome tool, a treatment and guidelines tool to provide data regarding treatments and guidelines for the selected disease, a medication tool, a randomize clinical trial tool, a pipeline agent tool to provide data on new and emerging therapies within a disease area, a pharmacists resources tool and/or a references tool.

The selected user type may be a nurse, and the associated one or more computer-implemented tools may include one or more of, for example, a nursing treatment goals tool, a nursing differential diagnosis and intervention tool, a medication tool, a complications tool, a health teaching tool, a nursing resources tool and/or a references tool.

The method may further include presenting a list of selectable commercially available devices relating to the one or more subject matters, and facilitating acquisition, by the user, of one or more of the devices in response to selection of the one or more devices by the user.

In another aspect, a system to manage presentation of information is disclosed. The system includes an audio-visual display device to present data, a processor-based computing device, and a storage device. The storage device is configured to store computer instructions that, when executed on the processor-based computing device, cause the processor-based computing device to retrieve information relating to one or more subject matters from one or more data repositories, the one or more subject matters including general non-personal information on medical conditions and treatments therefor, present on the audio-visual display device one or more sets of data from the retrieved information specific to a user type selected by a user from a plurality of user types, and present on the audio-visual display device another one or more sets of data from the retrieved information common to two or more user types selected from the plurality of user types.

Embodiments of the system may include any of the above-described features of the method.

In a further aspect, a computer program product residing on a computer readable storage device and comprising computer instructions is disclosed. The computer instructions, when executed on at least one processor-based device, cause the at least one processor-based device to retrieve information relating to one or more subject matters from one or more data repositories, the one or more subject matters including general non-personal information on medical conditions and treatments therefor, present on an audio-visual display device one or more sets of data from the retrieved information specific to a user type selected by a user from a plurality of user types, and present on the audio-visual display device another one or more sets of data from the retrieved information common to two or more user types selected from the plurality of user types.

Embodiments of computer program product may include any of the above-described features of the method and/or the system.

In yet another aspect, a method, performed by execution of computer readable program code by a processor of a computer system, for managing presentation of information is disclosed. The method includes retrieving information relating to one or more subject matters from one or more data repositories, the retrieved information including educational health care information, presenting one or more sets of data from the retrieved information specific to a user type selected by a user from a plurality of user types, and presenting another one or more sets of data from the retrieved information common to two or more user types selected from the plurality of user types.

Embodiments of the method may include any of the features of the above-described method, the system and/or the computer program product.

In a further aspect, a method, performed by execution of computer readable program code by a processor of a computer system, for managing presentation of information is disclosed. The method includes retrieving information relating to one or more subject matters from one or more data repositories, the one or more subject matters including health care information, presenting one or more sets of data from the retrieved information specific to a user type selected by a user from a plurality of user types including a physician, a nurse and a pharmacists, and presenting another one or more sets of data from the retrieved information common to all of the plurality of user types, the one or more sets of data common to all of the plurality of the user types includes background information relating to the one or more subject matters.

Embodiments of the method may include any of the features of the above-described methods, the system and/or the computer program product.

In another aspect, a method, performed by execution of computer readable program code by a processor of a computer system, for managing presentation of information is disclosed. The method includes retrieving information relating to one or more subject matters from one or more data repositories, the retrieved information including educational content, presenting one or more sets of data from the retrieved information specific to a user type selected by a user from a plurality of user types, the presented information arranged using a standardized presentation format to facilitate accessing the presented information using a set of pre-defined user-selectable items, and presenting another one or more sets of data from the retrieved information common to two or more user types selected from the plurality of user types.

Embodiments of the method may include any of the features of the above-described methods, the system and/or the computer program product.

In an additional aspect, a method, performed by execution of computer readable program code by a processor of a computer system, for managing presentation of information is disclosed. The method includes retrieving information relating to one or more subject matters from one or more data repositories, the one or more subject matters including continuing health education, presenting one or more sets of data from the retrieved information specific to a user type selected by a user from a plurality of user types, and presenting another one or more sets of data from the retrieved information common to two or more user types selected from the plurality of user types.

Embodiments of the method may include any of the features of the above-described methods, the system and/or the computer program product, as well as any of the following features.

The retrieved information may include medical, nursing and pharmacology continuing health education information at least partly developed by one or more of, for example, one or more pharmaceutical companies and/or one or more health care agencies.

Presenting the one or more sets of data from the retrieved information specific to the user type may include presenting the one or more sets of data from the retrieved information specific to the user type selected from a plurality of user types including a physician, a nurse and a pharmacist.

The retrieved information may include summaries of continuing information updates in relation to developments in health care.

In a further aspect, a method for managing presentation of information, performed by execution of computer-readable program code by a processor of a computer system, is disclosed. The method includes retrieving information relating to one or more subject matters from one or more data repositories, the one or more subject matters including general non-personal information on medical conditions and treatments therefor, presenting one or more sets of data from the retrieved information specific to a practitioner type selectable by a user from a plurality of practitioner types, presenting another one or more sets of data from the retrieved information common to two or more practitioner types selectable from the plurality of practitioner types, and presenting a further one or more sets of data from the retrieved information specific to at least one non-practitioner type.

Embodiments of the method may include any of the features described in the present disclosure, including any of the following features.

The one or more subject matters may include health care.

The plurality of practitioner types may include one or more of, for example, a physician, a nurse, a pharmacists, a physician assistant, a doctor of osteopathy, a paramedic/emergency medical technician (EMS), a registered practical nurse, a nursing aide, and/or a health care student. The at least one non-practitioner type may include a patient.

Presenting the other one or more sets of data common to the two or more practitioner types may include displaying on a display device a landing page identifying at least one of the two or more practitioner types, the at least one non-practitioner type, and the one or more subject matters, the landing page including user selectable items respectively associated with the at least one of the two or more practitioner types and the at least one non-practitioner type.

The method may further include presenting on the landing page, in response to selection of one of the user selectable items identifying the at least one of the two or more practitioner types, a menu including a listing of topics relating to the one or more subject matters, and presenting, when a selectable topic from the listing of topics is associated with one or more drill-down levels of sub-menus of sub-topics relating to the selectable topic, one of the one or more drill-down levels in response to selection of an item from a sub-menu of a preceding drill-down level associated with the selectable topic and with the one of the one or more drill-down levels of sub-menus.

The listing of topics may include a listing of health care topics, and the one of the one or more drill-down sub-menus may include a list of diseases associated with the selected topic.

The method may further include presenting, in response to selection of a disease from the list of diseases associated with the selected topic, a disease detail page containing data specific to the selected disease.

Displaying the topics page may include presenting an interactive model including graphical data relating to at least one topic from the listing of topics relating to health care.

The model may include a composite of graphical layers that are each representative of different anatomical structures of the human body. At least one of the graphical layers may be configured to be interactively displayed or suppressed.

Presenting the disease detail page may include, when the practitioner-type is selected from the plurality of practitioner types, presenting a first area including user selectable items common to the two or more practitioner types, presenting a second area including user selectable items specific to the selected practitioner type, and presenting a third area including data relating to the selected disease retrieved in response to selection of one of the user selectable items from the first area or the second area. When the at least one non-practitioner type is selected, presenting the disease detail page may include presenting a disease definition and causes icon, a symptom icon, an investigation and treatment icon, a risk factor and prevention icon, and an outcome icon.

The user selectable items common to the two or more practitioner user types may include a disease definition icon, an epidemiology icon, a pathophysiology icon, an etiology icon and a clinical presentation icon.

The method may further include displaying, in response to selection of one of the user selectable items identifying the at least one of the two or more practitioner types, a topics page including a listing of topics relating to the one or more subject matters.

The method may further include presenting a tools menu identifying one or more computer-implemented tools to perform one or more of, for example, accessing available data and/or processing the available data.

When the practitioner type is selected, the one or more computer-implemented tools may include a Continuing Health Education tool implemented for a topic selected from a listing of topics presented in a topics page to present to the user educational materials relating to the selected topic, a Presentation Builder tool to construct a presentation based on one or more of an audio data and visual data to be provided to the user, an All Video tool to present videos relating to the topic selected from the listing of topics presented in the topics page, an Audio and Podcast tool to present audio data relating to the topic selected from the listing of topics presented in the topics page, and a Charts and Graphs tool to present graphical information relating to the topic selected from the listing of topics presented in the topics page.

When the non-practitioner type is selected, the one or more computer-implemented tool may include a Brochures/Pamphlets tool configured to provide the non-practitioner type user with additional information about a selected disease; a Do's & Don't's tool configured to present information about healthy choices and compliance with medications, a Diet tool configured to present information regarding dietary choices, a Log book tool configured to provide a downloadable outline for guidance to patients to track and monitor specific health issues, the health issues including one or more of, for example, dietary changes, exercise, weight and blood pressure measurements, and/or medication side effects, and a Videos tool configured to present educational videos on specific disease areas.

The method may further include presenting, when the practitioner type is selected, a quick review selectable item that, when selected, causes the presentation of an executive summary of one or more selected diseases in table format.

The method may further include presenting, when the non-practitioner type is selected, a patient health profile selectable item that, when selected, enables performing one or more of, for example, recording and maintaining user-specific health information, and/or recording and maintaining user non-specific supplemental health information.

In another aspect, a system to manage presentation of information is disclosed. The system includes an audio-visual display device to present data, a processor-based computing device, and a storage device to store computer instructions. The computer instructions, when executed on the processor-based computing device, cause the processor-based computing device to retrieve information relating to one or more subject matters from one or more data repositories, the one or more subject matters including general non-personal information on medical conditions and treatments therefor, present one or more sets of data from the retrieved information specific to a practitioner type selectable by a user from a plurality of practitioner types, present another one or more sets of data from the retrieved information common to two or more practitioner types selectable from the plurality of practitioner types, and present a further one or more sets of data from the retrieved information specific to at least one non-practitioner type.

Embodiments of the system may include any of the features described in the present disclosure, including any of the features described above in relation to the method, and the features described below.

The computer instructions may further include instructions that, when executed on the processor-based computing device, further cause the processor-based computing device to present, when the practitioner type is selected, a quick review selectable item that, when selected, causes the presentation of an executive summary of one or more selected diseases in table format, and to present, when the non-practitioner type is selected, a patient health profile selectable item that, when selected, enables performing one or more of, for example, recording and maintaining user-specific health information, and/or recording and maintaining user non-specific supplemental health information.

In an additional aspect, a computer program product residing on a computer readable storage device and comprising computer instructions is disclosed. The computer instructions, when executed on at least one processor-based device, cause the at least one processor-based device to retrieve information relating to one or more subject matters from one or more data repositories, the one or more subject matters including general non-personal information on medical conditions and treatments therefor present one or more sets of data from the retrieved information specific to a practitioner type selectable by a user from a plurality of practitioner types, present another one or more sets of data from the retrieved information common to two or more practitioner types selectable from the plurality of practitioner types, and present a further one or more sets of data from the retrieved information specific to at least one non-practitioner type.

Embodiments of the computer program product may include any of the features described in the present disclosure, including any of the features described above in relation to the method and the system.

Details of one or more implementations are set forth in the accompanying drawings and in the description below. Further features, aspects, and advantages will become apparent from the description, the drawings, and the claims.

BRIEF DESCRIPTION OF THE DRAWINGS

FIG. 11 is an image of an interface page that includes an All Charts and Graphs tool.

FIG. 15 is an image of another example detail page configured to enable interaction by, and access to data for, practitioner and/or non-practitioner user types.

FIG. 16 is table-formatted executive summary generated, for example, by activating a Quick Review feature.

FIG. 17 is an image of a patient-specific disease detail page.

FIG. 18 is an example of a Patient Health Profile.

Like reference numbers and designations in the various drawings indicate like elements.

DETAILED DESCRIPTION

Disclosed are systems, methods and articles for managing presentation of information. Embodiments include a method, performed by execution of computer readable program code by a processor of a computer system, that includes retrieving information relating to one or more subject matters from one or more data repositories. In some embodiments, the one or more subject matters may include general non-personal information on medical conditions and treatments therefor. The method also includes presenting one or more sets of data from the retrieved information specific to a user type selected by a user from a plurality of user types, and presenting another one or more sets of data from the retrieved information common to two or more user types selected from the plurality of user types.

In some implementations, the information (relating to one or more subject matters) that is retrieved includes educational health care information. In some implementations, the retrieved information is presented to a user type selected from a plurality of user types that includes a physician, a nurse and a pharmacist, while some of the data from the retrieved information are presented to all of the plurality of user types.

In some implementations, disclosed is a method for managing presentation of information that includes retrieving information relating to one or more subject matters from one or more data repositories, the one or more subject matters including general non-personal information on medical conditions and treatments therefor, presenting one or more sets of data from the retrieved information specific to a practitioner type selectable by a user from a plurality of practitioner types, presenting another one or more sets of data from the retrieved information common to two or more practitioner types selectable from the plurality of practitioner type, and presenting a further one or more sets of data from the retrieved information specific to at least one non-practitioner type.

In some implementations, the retrieved information includes educational content, and the presented information is arranged using a standardized presentation format to facilitate accessing the presented information using a set of pre-defined user-selectable items. In some embodiments, the retrieved information pertains to one or more subject matters that include continuing health education.

Figure 1:
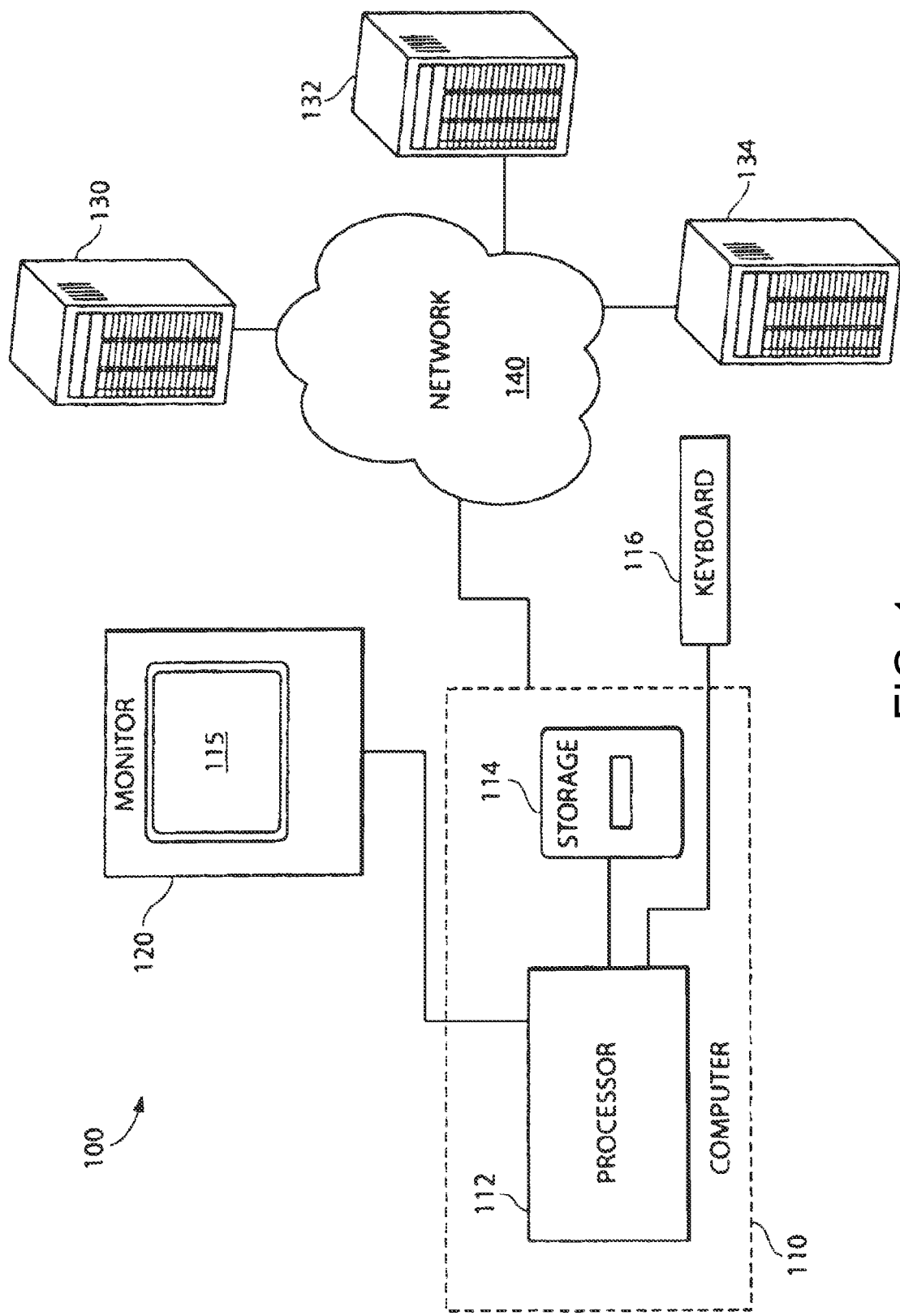
FIG. 1 is a schematic diagram of an implementation of an information presentation management system.

With reference to FIG. 1, a schematic diagram of an implementation of an information presentation management system 100 is shown. The information presentation management system 100 includes at least one processor-based device 110 such as a personal computer (e.g., a Windows-based machine, a Mac-based machine, a Unix-based machine, etc.), a specialized computing device, and so forth, that typically includes a central processor unit 112. In some embodiments, the processor-based device may be implemented in full, or partly, using an iPhone™, a Blackberry™, an Android-based phone, or some other portable device (e.g., smart phone device), that can be carried by a user, and which may be configured to perform remote communication functions using, for example, wireless communication links (including links established using various technologies and/or protocols, e.g., Bluetooth). In addition to the CPU 112, the system includes main memory, cache memory and bus interface circuits (not shown). The processor-based device 110 includes a mass storage element 114. The mass storage element 114 may be, for example, a hard drive associated with personal computer systems.

Implemented on the information presentation management system 100 is a user interface 115 to present and/or manage content on a display device 120 (an audio-visual display device), e.g., a CRT (cathode ray tube) or LCD (liquid crystal display) monitor. The user interface 115, also referred to as a portal, is used to present information relating to one or more subject matters based, at least in part, on input provided by the user, for example, through a keyboard 116. Other modules that may be included with the system 100 are speakers and a sound card (used in conjunction with the display device to constitute the user output interface), a pointing device, e.g., a mouse, a trackball or a touch-based GUI (used in conjunction with the keyboard to constitute the user input interface) by which the user can provide input to the information presentation management system 100.

The processor-based device 110 of the information presentation management 100 is configured to facilitate, for example, the implementation of data retrieval, management and presentation operations such that certain portions of data, when presented on the interface 115 of the data presentation management system, are generally intended for viewing by one user type, while other portions of data are available to be retrieved and viewed by two or more (and, in some cases, all) the user types using the data presentation management system. In some embodiments, the two or more user types are practitioner types, where the system 100 also enables non-practitioner type user to view some information. For example, and as will be described in greater detail below, one type of a health care practitioner, e.g., a doctor, may be able to make selections (via drill-down functionality of the interface, implemented through a single page or through multiple pages) that would direct that user to screens/pages that include, in one area of the interface, data generally intended for viewing by doctors (e.g., scientific publication about medical advancement and research in relation to a particular medical condition, details about intricate medical procedures and therapies to treat the particular medical condition, etc.), and also include, for example, in another area, data (e.g., background information and summaries about a particular medical condition, symptoms of the medical condition, etc.) that is not necessarily specific to physicians, but may be viewed and used by two or more types of health practitioners The storage device 114 may include computer program products that, when executed on the at least one processor-based device 110, perform operations to facilitate the implementation of the data presentation management procedures, including implementation of an interface that enables presentation of one or more data sets specific to a user type selected by a user, and present another one or more data sets of retrieved information that are common to two or more user types.

The processor-based device may further include peripheral devices to enable input/output functionality. Such peripheral devices include, for example, a CD-ROM drive, a flash drive, or a network connection, for downloading related content to the connected system. Such peripheral devices may also be used for downloading software containing computer instructions to enable general operation of the respective system/device, as well as to enable data retrieval from local or remote data repositories and presentation and management of data. Alternatively and/or additionally, in some embodiments, special purpose logic circuitry, e.g., an FPGA (field programmable gate array) or an ASIC (application-specific integrated circuit) may be used in the implementation of the information presentation management system 100. The at least one processor-based device 110 may include an operating system, e.g., Windows XP® Microsoft Corporation operating system. Alternatively, other operating systems could be used. Additionally and/or alternatively, one or more of the procedures performed by the data presentation management system may be implemented using processing hardware such as digital signal processors (DSP), field programmable gate arrays (FPGA), mixed-signal integrated circuits, etc. In some embodiments, the processor-based device 110 may be implemented using multiple inter-connected servers (including front-end servers and load-balancing servers) configured to store information pulled-down, or retrieved, from remote data repositories hosting content that is to be presented on the interface 115.

The various systems and devices constituting the system 100 may be connected using conventional network arrangements. For example, the various systems and devices of system 100 may constitute part of a public (e.g., the Internet) and/or private packet-based network. Other types of network communication protocols may also be used to communicate between the various systems and devices. Alternatively, the systems and devices may each be connected to network gateways that enable communication via a public network such as the Internet. Network communication links between the systems and devices of system 100 may be implemented using wireless or wire-based links. For example, in some embodiments, the system may include communication apparatus (e.g., an antenna, a satellite transmitter, a transceiver such as a network gateway portal connected to a network, etc.) to transmit and receive data signals. Further, dedicated physical communication links, such as communication trunks may be used. Some of the various systems described herein may be housed on a single processor-based device (e.g., a server) configured to simultaneously execute several applications. As will be described in greater detail below, in some embodiments, the information presentation management system 100 may retrieve data from one or more remote servers that host data repositories of the one or more subject matters with respect to a user accesses information presented on the interface 115. FIG. 1 depicts three servers 130, 132 and 134 from which the system 100 may retrieve data. Additional or fewer servers may be used with the system 100. The system 100 and the servers 130, 132 and 134 are interconnected via a network 140.

Figure 2A:
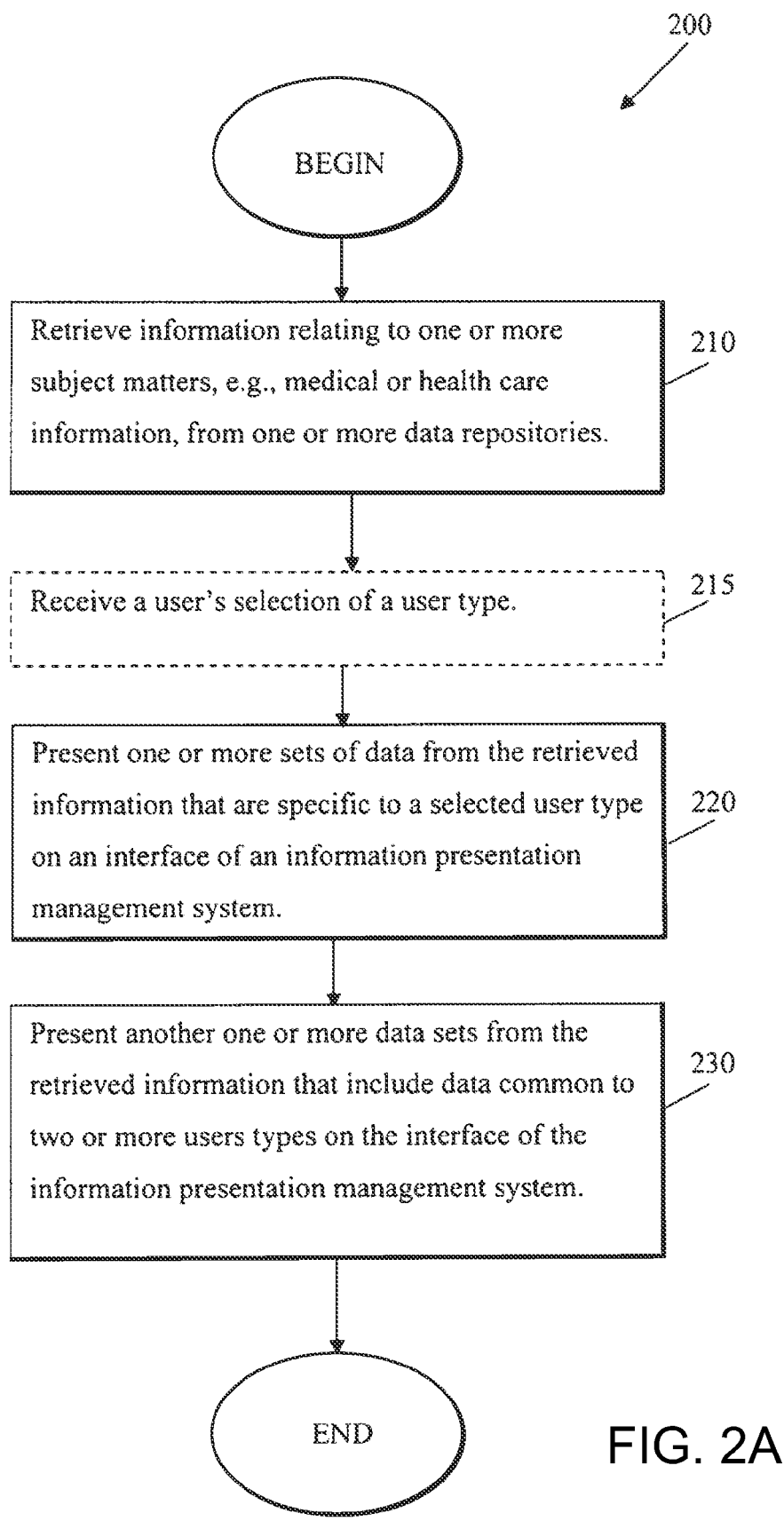
FIG. 2A is a flow chart of a procedure to manage presentation of information (e.g., medical information).

Referring to FIG. 2A, a flow chart of a procedure 200 to manage presentation of information (e.g., medical information) is shown. Generally, a user having access to a computing device may access the information to be managed from a remote location, such as one or more computer servers (like the servers 130, 132 and/or 134) used to implement a data repository. The repository may thus be implemented as a distributed system of data repositories with some data maintained on a server located in one location, and other data located elsewhere. For example, in relation to medical information repository, one or more pharmaceutical companies may maintain a data repository with data relating to medications and/or other therapies, another entity (an association of physicians) may maintain a repository of continuing health education materials, and yet a further entity may maintain a repository of data on medical conditions and recent publications and research pertaining to those conditions.

A user wishing to access information about one or more subjects matters, for example, medical or health care information, launches from his/her computing device the interface through which the information is to be presented. In some embodiments, the interface may be implemented as a webpage presented on conventional web browser executing from the user's station. Under those circumstances, the data repository (or repositories) accessed by the user's station may include a web server that, upon being accessed by the user's station, transmits web-based content, e.g., data formatted in a markup language, such as hypertext markup language (HTML) and/or Extended Markup Language (XML). In such implementations, the accessed server may retrieve data requested by the user from a local storage device or from remote storage device (in situation for the data repository is implemented as a distributed system), format the data content using, for example, one or more types of markup languages, and transmit the formatted data back to the user's station on which the system and interface is operating.

Where implemented on an Internet browser, such as Internet Explorer™, the entire presentation of the interface may be rendered within the display area of the browser. The content to be presented on the interface may thus be specified using, for example, Semantic HTML syntax. In some embodiments, JavaScript, or some other scripting language, may be used to control the behavior and operation of the interface. Additionally, implementation of the interface may also be realized using programmable web browser plugins (e.g., Adobe Flash. Microsoft Silverlight, etc.)

In some embodiments, the user interface may be implemented as a dedicated software application, e.g., a proprietary software implementation developed to enable presentation of content retrieved from one or more data repositories. The interface can thus be implemented, for example, as an application window operating on an MS-Windows platform, or any other type of platform that enables implementation of graphical user interfaces. In circumstances where the interface is implemented as a window, the interface can be designed and presented using suitable programming languages and/or tools, such as Visual Basic, that support the generation and control of such interfaces. Where a dedicated software application is developed to implement the system and its interface, the retrieved data may be formatted or coded to enable the data's presentation in the desired manner, for example, in the manner to be described in greater detail below.

Thus, information relating to one or more subject matters, e.g., medical or health care information, is retrieved 210 from one or more data repositories. The data retrieved includes multiple data sets that are used to populate screens/pages presented on the user interface in some order that may be based on, at least in part, the selected user type, other selections made by the user via the interface, etc. Data may be transmitted as batches of one or more data sets corresponding to the one or more screens that are to be viewed by the user. Subsequent data sets (e.g., corresponding to subsequent screens) may be retrieved in response to user selections of more specific data requests or in response to new request for different type of information (e.g., relating to a different subject matter). Additionally and/or alternatively, in some embodiments, data transfer may be more extensive to enable a more expeditious processing of data retrieval in response to user's input. For example, in response to a user's request for information in relation to a particular subject matter, a comprehensive data transfer of a significant portion of the data stored on a remote server with respect to that subject matter may be initiated so that much of the data the user may wish to access becomes locally stored (at least temporarily).

As noted, in some embodiments, the user interface is configured as a "drill-down" interface such that the user can navigate through the retrieved data by selecting progressively more specific user selectable items (e.g., icons, links, selections buttons, text fields, etc.) Such drill-down functionality may be implemented by selecting an item, such as a topic, from a list of items, to cause another, different page to be presented, with such a page including additional, more specific, sub-items associated with the selected item from the previous page. Additionally and/or or alternatively, as will be described below in greater detail, in some embodiments, the drill-down functionality may be implemented, at least in part, by presenting sub-menus on the same page from which the more general item was first selected. As further noted, at least some of the content (e.g., particular screens/pages) presented in response to certain user selections may include some data unique to a specific user type, while some content (for example, on a particular screen/page) may be common to two or more user types. Thus, and with continued reference to FIG. 2A, one or more sets of data from the retrieved information that are specific to a user type, selected from a plurality of user types by, for example, the user using the interface, are presented 220 on the interface of the information presentation management system 100. Additionally, another one or more data sets from the retrieved information that include data common to two or more, and in some cases all, the users types, are presented 230. As will become apparent below, in some instances a display screen presented on the interface will include data specific to the selected user type, as well as data common to two or more user types.

As further shown in FIG. 2A, in some implementations, the user using the information presentation management system and interacting via the interface selects the user type with respect to which data content specific to that user type may be presented at that time instance or at subsequent time instances (e.g., presented in subsequent screens/pages). Thus, a user's selection of a user type is received 215, and based on that selection (and/or on further selections regarding the particular information sought), additional content to be presented may be retrieved and presented on the current screen or in subsequent screens.

Figure 2B:
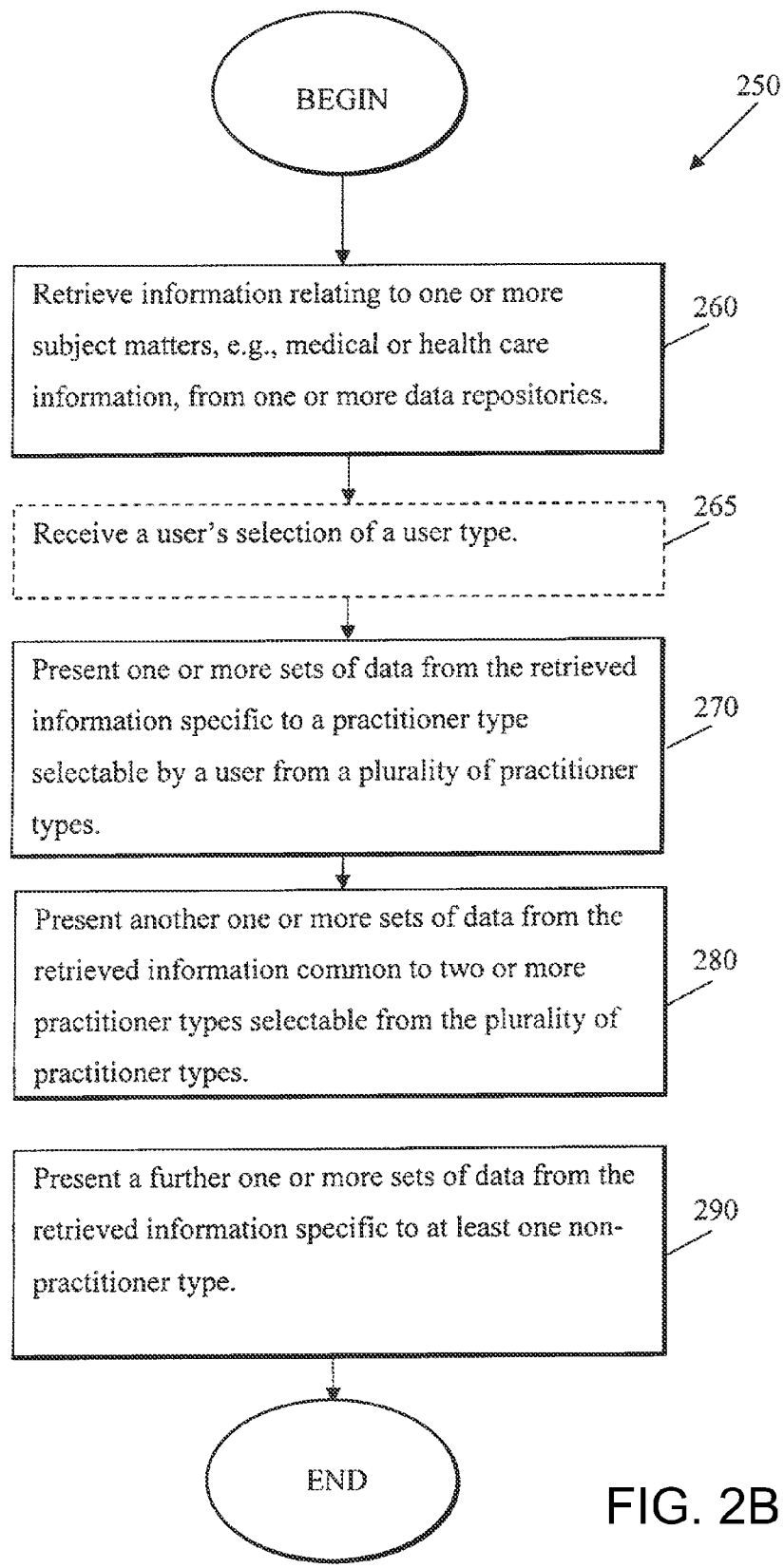
FIG. 2B is a flowchart of another example procedure to present content (e.g., content relating to health care subject matters).

With reference to FIG. 2B, a flowchart of another example procedure 250 to present content (e.g., content relating to health care subject matters) is shown. The procedure 250 may generally be similar to the procedure 200 of FIG. 2A, but may also include the functionality that content specific to a non-practitioner user types (e.g., a patient) could be presented. A non-practitioner user type generally does not, in some embodiments, directly share, or is allowed access to, the information shared by practitioner type user. For example, health-care practitioners accessing content through the system 100 will be provided with information and details (e.g., in relation to disease, health conditions, therapies etc.) that would generally not be provided to a patient. Instead, in some embodiments, a patient may be able to navigate to pages having content to provide lay-person information about the subject matter available through selection of one or more of several user selectable items (icons).

Thus, in performing the procedure 250, information relating to one or more subject matters (e.g., health care) is retrieved 260 from one or more data repositories, with the one or more subject matters including general non-personal information on medical conditions and treatments therefor. Similarly to the procedure 200, the data retrieved includes multiple data sets that are used to populate screens/pages presented on the user interface in some order that may be based on, at least in part, the selected user type (be it a practitioner user type, or non-practitioner user type, other selections made by the user via the interface, etc.) Data may be transmitted as batches of one or more data sets corresponding to the one or more screens that are to be viewed by the user. Subsequent data sets (e.g., corresponding to subsequent screens) may be retrieved in response to user selections of more specific data requests or in response to new request for different type of information (e.g., relating to a different subject matter).

Subsequently, one or more sets of data from the retrieved information specific to a practitioner type, selectable from a plurality of practitioner types, is presented 270. For example, and as will be described in greater details below (e.g., in relation to FIGS. 3A and 3B), a user may be provided with several selectable items associated with different practitioner-types. The selection of one of those practitioner types (which, in some implementations, may be an automatic selection based on information associated with the user that is retrieved or determined when logging on to the system 100) may cause data specific to the selected practitioner type to be presented (e.g., a doctor may be presented with information regarding possible therapies available to treat a patient, whereas other practitioner-type users may be provided with different information). In some embodiments, the selection of the user type is performed 265 by the user. Another one or more data sets from the retrieved information that include data common to two or more practitioner types (selectable from the plurality of practitioner types) are presented 280.

Figure 3A:
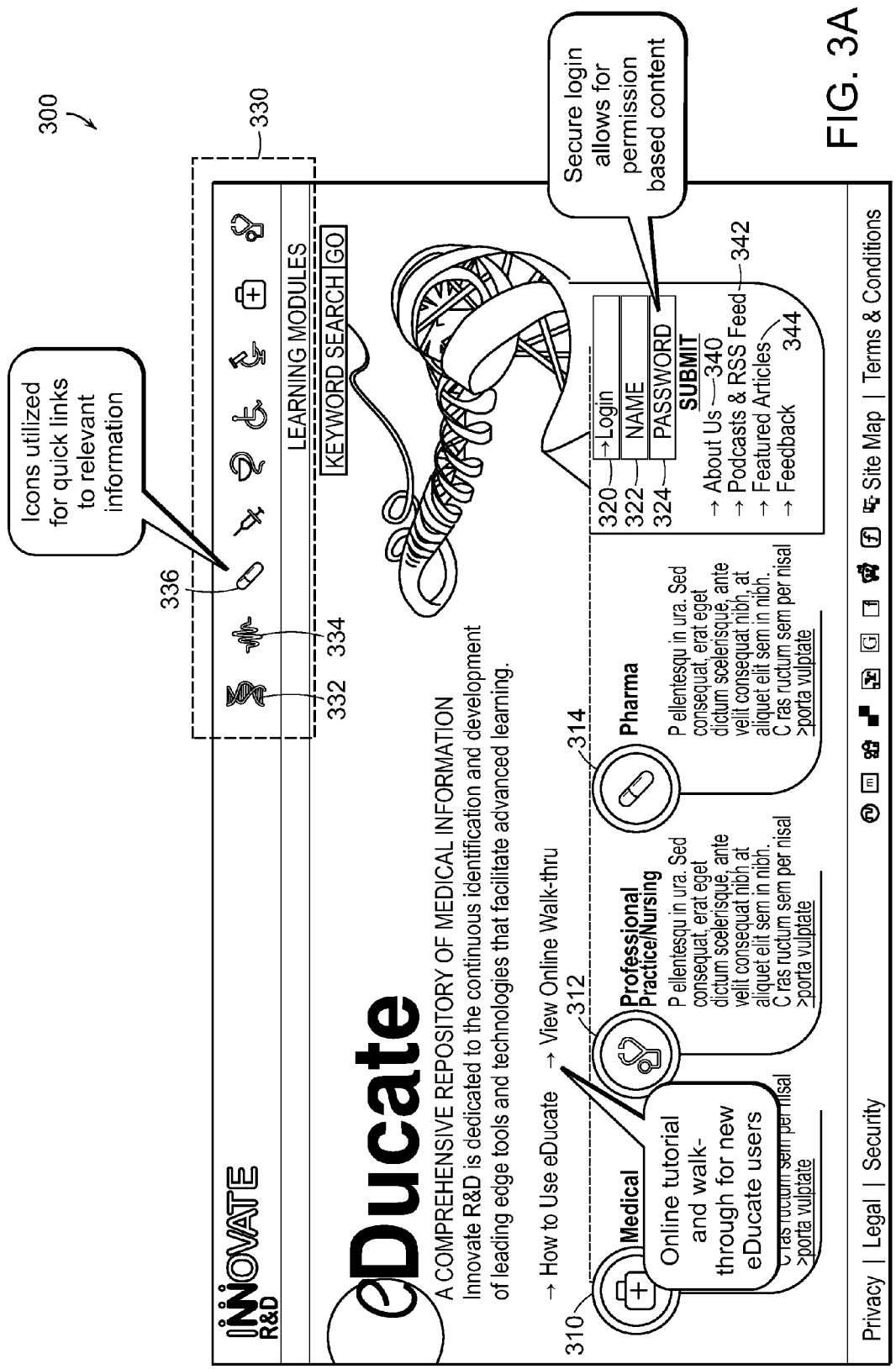
FIG. 3A is an image of a landing page that includes user selectable items to enable selection of the user type.

Additionally, as shown in FIG. 2B, a further one or more sets of data from the retrieved information that are specific to at least one non-practitioner type (e.g., a patient, where the subject matter is related to health care) is presented 290. In some embodiments, the selection of the specific user type is performed from a "landing" page that includes user selectable items, for example, selectable graphical icon, identifying at least one user type. The user can, for example, click on an appropriate icon corresponding to the user type with respect to which information specific to that user type is to be presented. Referring to FIG. 3A, an image of a landing page 300 that includes user selectable items to enable selection of the user type is shown. The landing page 300 includes user selectable items 310, 312, 314, in this case, selectable graphical icons that the user can select by clicking the appropriate icon, to specify the user type with respect to which information specific to that selected user type will be retrieved and presented (in conjunction with, at least for some screens/pages, information common to two or more user types).

In the implementation depicted in FIG. 3A, the interface is configured to present medical information, with the selectable items 310, 312, 314 corresponding to Medical practitioners, e.g., physicians, Professional Practice practitioners, e.g., nursing, and Pharma practitioners, e.g., pharmacists. Additional icons corresponding to additional user types (e.g., for health practitioners, this may also include, for example, icons for a physician assistant, a doctor of osteopathy, a paramedic/emergency medical technician (EMS), a registered practical nurse, a nursing aide, a health care student, etc.) may also be made available. In some embodiments, a description of what the interface will enable for each of the available user types is provided.

As further shown, the landing page 300 may also have a login area 320, including a name and password fields 322 and 324, respectively, to enable permission-based content to be accessed by the logging user. For example, some of the data stored on the data repository may be accessed only if the user has the proper authorization to access this type of data. Under those circumstances, a user logging onto the information presentation management system may be directed, after the system completes the login procedure and/or a user authentication procedure, to another top-level screen, from which the logged-in user may further navigate to access-restricted data. The system 100 may store profiles of the logging users that include indicators of the user-types associated with the respective logging users. For example, a physician logging into the system would be recognized by the system as a physician with an associated physician user type designation and with an associated permission level, to thus enable presentation of appropriate information to that logging user.

In some embodiments, screens of the interface (portal) may include several content-selection selectable items such as content icons 330, also referred to as quick-link icons, shown at the top right corner of the screen 300. By selecting any one of the content icons, the user can more quickly drill-down to certain categories of information. For example, the "DNA" icon 332 directs a user to pathophysiology information, the "EKG/ECG" icon 334, for example, directs the user to presentation of investigations information, the "pill" icon 336 directs the user to information pertaining to treatments and guidelines, and so on. Selection of any of the quick-link icons in conjunction with previous and/or subsequent user selections (e.g., of particular topics) thus enables the user to quickly present information the user is looking for without having to traverse at least some of the pages presentable on the interface 115. Thus, once the user becomes familiar with the simpler quick link icons, searching and "drilling down" to access relevant information can be performed relatively quickly. These quick-link icons may also be displayed in other screens to enable the user quick access to general information from various points in the interface as the user is navigating through the interface. In some embodiments, the quick link icons may be configured to present, in response to their selection, succinct summaries of information within a category. For example, clicking on the pill icon 336 may cause presentation of treatments and guidelines (for general broad categories, or for narrower categories in accordance with other user selections) as single word lists from which the user could then select his/her choice for further expansion and elaboration. In circumstances where the user-type has been specified, selection of the quick-link topic icons directs the user to general information that may be specific to that user type. Accordingly, the user interface is configured to present, in response to user selection of a quick link topic and based on the specified user-type, general information corresponding to that quick link topic and the specified user-type.

With continued reference to FIG. 3A, in some embodiments the landing page 300 may also include a user selectable item 340, annotated "About Us" to provide users with information about the interface (e.g., version number, etc.) Also included is an RSS icon 342 to direct users to another screen of the portal from which Really Simple Syndication sites, providing podcasts and current information about the one or more subject matters being accessed via the interface. The interface may therefore be configured to present RSS feeds accessed via such a page. In some embodiments, the RSS links that are made available may be based on the user-type specified and/or on a profile associated with a specific user logging into the system to access customized and/or permission-based information. Also included on the landing page 300 is a "Featured Articles" icon 344 that directs the user to a page with links and/or content of publications relevant to the one or more subject matters for which retrieved data is to be processed and presented on the interface, and/or relevant to the specific user-type that may have been previously selected.

In some implementations, the landing page may include a ticker (continuous/flowing or intermittent) to provide information on emerging continuing health education (CHE) programs, podcasts, video, and CHE programs that are available on the website. The ticker may be placed in proximity to a key word search area so one might be able to type in a particular medical/learning/drugs/pharmacy term to allow a hyperlink to that section of the learning module.

Figure 3B:
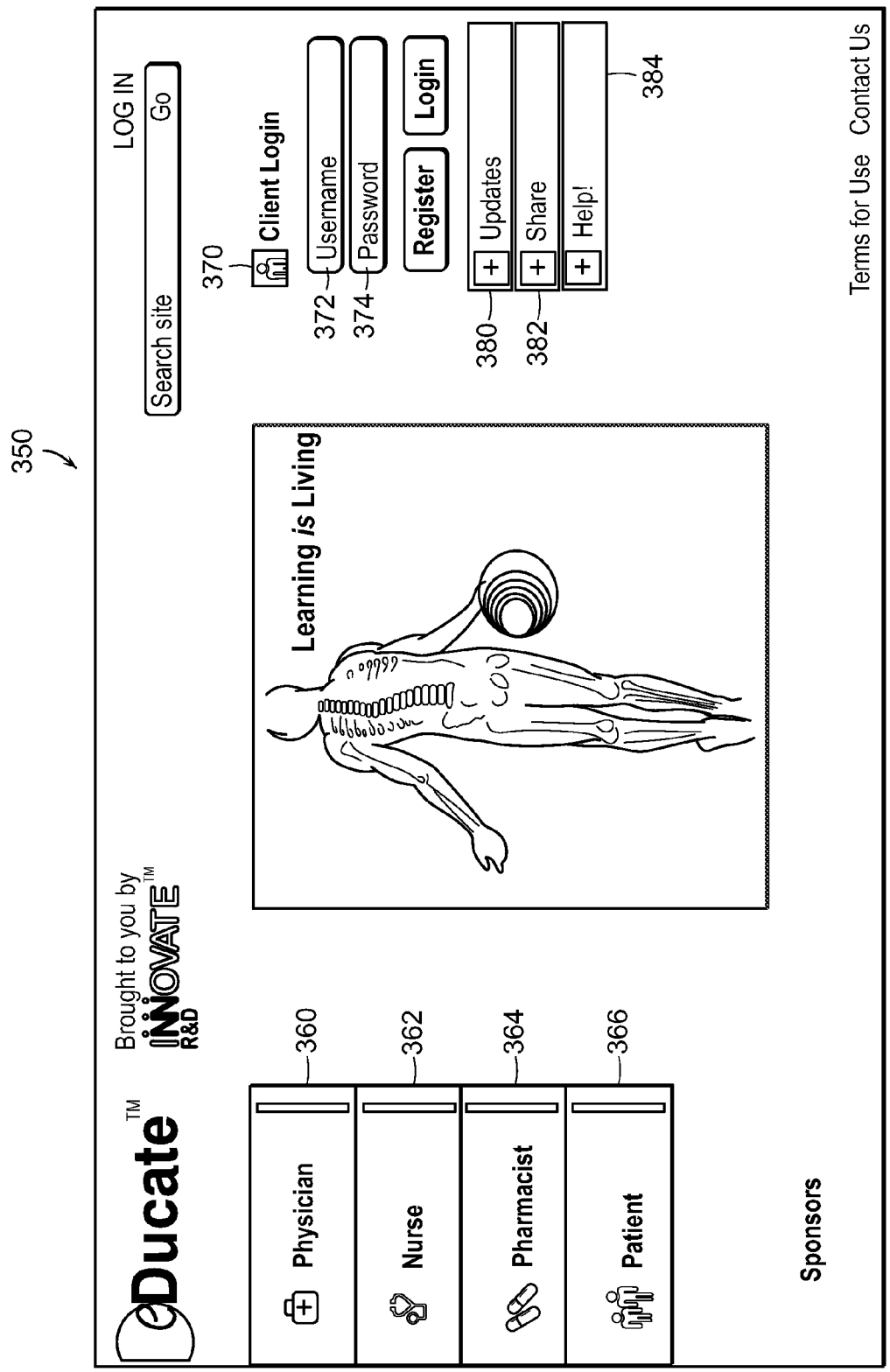
FIG. 3B is an image of another example landing page that includes user selectable items to enable selection of a user type from one or more practitioner user types and from one or more non-practitioner user types.

FIG. 3B is an image of another example landing page 350 that includes user selectable items to enable selection of a user type from one or more practitioner types, and from one or more non-practitioner types. The landing page 350 includes user selectable items 360, 362, 364, corresponding to practitioner user types (e.g., physician, nurse, and pharmacist) that the user can select by, for example, clicking the appropriate icon, to specify the user type with respect to which information specific to that selected user type will be retrieved and presented (in conjunction with, at least for some screens/pages, information common to two or more practitioner types). Selectable items for other practitioner types may also be included. Additionally, the landing page 350 also includes a user selectable item 366 corresponding to a non-practitioner user type, e.g., a patient. In response to selection of one of the practitioner-type selectable items, information specific to that selected practitioner user type, as well as information common to two or more of the practitioner types, may be retrieved and presented. In response to selection of the selectable item corresponding to the non-practitioner type (e.g., by clicking or hovering over the selectable item, which in the example landing page 350 is the selectable item 366).

As with the landing page 300 of FIG. 3A, the landing page 350 may also have a login area 370, including a name and password fields 372 and 374, respectively, to enable permission-based content to be accessed by the logging user. Thus, a user logging onto the information presentation management system may be directed, after the system completes the login procedure and/or a user authentication procedure, to another top-level screen, from which the logged-in user may further navigate to access-restricted data. The system 100 may store profiles of the logging users that include indicators of the user-types associated with the respective logging users. For example, a non-practitioner user logging into the system would be recognized by the system as a non-practitioner with an associated non-practitioner user type designation and with an associated permission level, to thus enable presentation of appropriate information to that logging non-practitioner user.

As further shown, the landing page 350 include expandable selectable items 380, 382, and 384, corresponding to selectable items for "Updates," "Share," and "Help!," respectively. When selected, the Share icon 382, for example, enables a user to reveal a list of one or more communication applications (e.g., twitter, MSN messenger, Facebook, etc.) In response to selection of one of those communication applications, the selected application becomes active, enabling the user to add a comment to be communicated to the intended recipients, attach some or all of the information being presented on the interface 115, or otherwise perform other functions to communicate with other users. Upon completion of the user operations on the one or more selected applications, the content of the communications is forwarded to the intended recipients. The tool may be accessible from other pages. In some embodiments, the Update feature (activated, for example, by selection of the Update icon 380) may be used to provide updates as to (i) what is new on the website (e.g., the Innovate™ website, implemented using the system 100, and including interface pages similar to those shown herein), (ii) inform when new topics will be or have been released, and (iii) when any new teaching material (CHE, Clinical trial info, Videos etc) will be or have been uploaded. The Update feature/tool may be accessible from other pages.

Although not shown in the example landing page 350 of FIG. 3B, in some implementations, a landing page that also enables a non-practitioner user type to access data through the system 100 may include at least some of the features provided in the example landing page 300 of FIG. 3A. For example, the landing page may also include such features as quick-link icons to quickly drill-down to certain categories of information (e.g., icons such as the "DNA" icon 332, the "EKG/ECG" icon 334, etc. of FIG. 3A), an "About Us" user selectable (such as the item 340 of FIG. 3A) to provide users with information about the interface, an RSS icon (similar to the icon 342 of FIG. 3A) to direct users to another screen of the portal from which Really Simple Syndication sites, a "Featured Articles" icon (similar to the icon 344 of FIG. 3A) that directs the user to a page with links and/or content of publications, a ticker (continuous/flowing or intermittent) to provide information on emerging continuing health education (CHE) programs, podcasts, video, and CHE programs that are available on the website, etc.

As noted, in response to a selection (e.g., by clicking) of one or more of the user selectable items corresponding to a plurality of user types, such as Medical (e.g., doctor), professional practice (e.g., nurses), or pharmacy, the interface drills down to a sub page that, in some embodiments, provides information and/or additional selectable options, with at least some of additionally presented information and/or user selectable items being predicated on the specific user type selected.

Figure 4:
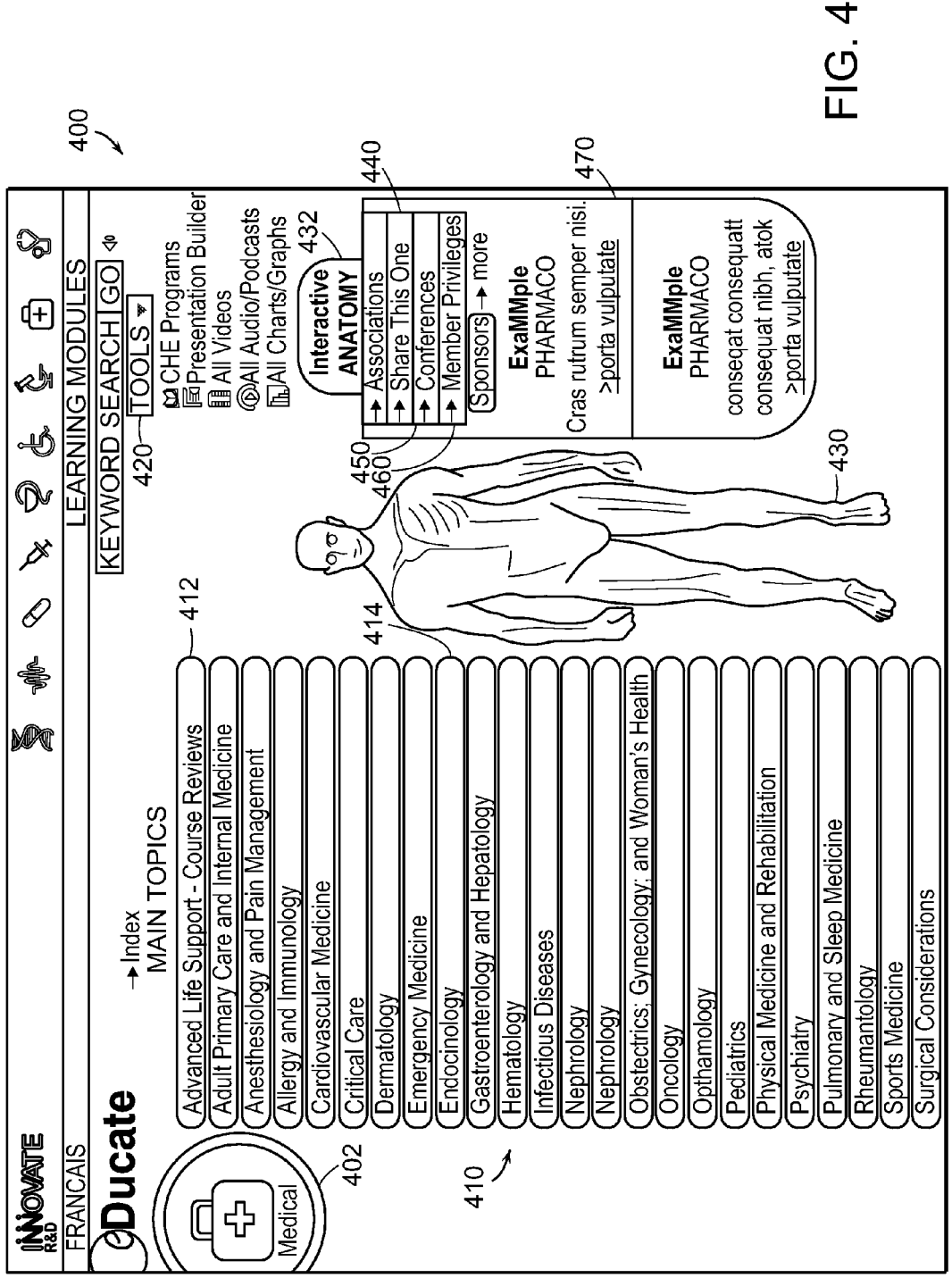
FIG. 4 is a topics sub-landing page that includes a listing of topics relating to the one or more subject matters.

Thus, and with reference to FIG. 4, in some embodiments, in response to selection of a user type from the page 300, a "topics" sub-landing page 400 that includes a listing of topics 410 relating to the one or more subject matters is presented. The information presented in this page may include at least some data sets that are specific to the user-type earlier selected. As shown in the top-left area of the topics page 400, the user-selectable item 402 corresponding to "Medical" (identifying the user-type of physicians) is prominently displayed, indicating that the user has selected this user type in a preceding page (e.g., at page 300), and that at least some of the data retrieved and presented is data specific to "Medical" user-type. In some embodiments, the topics pages may include information that is common to two or more (or even all) of the user types from the plurality of user types that are to use the information presentation management system, and only upon further selection of options via user selectable items presented on that page would information specific to the selected user type be retrieved and presented on the interface.

As shown in FIG. 4, the topics page 400 lists twenty four (24) main topics of medicine that the user can select from. In circumstances where the interface is to present information pertaining to health care (or health education), the topics listed on the topics page 400 include associated health care topics.

One example of a topic for selection that may be available to health professionals is the topic 412 of "Advanced Life Support (ALS)—Course Review". Selection of the ALS topic 412 causes the retrieval and presentation of specific courses on advanced cardiac life support (ACLS), advanced trauma life support (ATLS), and advanced stroke life support (ASLS).

With respect to the above-identified critical care sub-topics, the ALS topic may provide, for example, an overview of acute management of stroke patients including administration of intravenous tissue plasminogen activator (tPA) with inclusion and exclusion criteria and medical management with regards to hypertension, hypoglycemia, fluid balance, oral intake, fever, elevated white count, bowel and bladder dysfunction, arrhythmias including atrial fibrillation, etc. The program would also include neuroimaging with CT, CT angiogram, MRI, MR angiogram, carotid ultrasound, transcranial Doppler ultrasound, ECG, and telemetry recordings, as well as addressing metabolic derangements in terms of electrolytes, glucose, thrombocytopenia, thrombocytosis, anemia. In addition, the risks and benefits of interventional therapy (intra-arterial tPA, clot retrieval devices, angioplasty with or without stenting, hemi-craniectomies and carotid endarterectomy) could be described. Hemorrhagic stroke would also be addressed from the stand point of subarachnoid hemorrhage and aneurysmal rupture, and administration of appropriate therapy, work up and investigations as well as management. Intra-parenchymal hemorrhages would also be dealt with in a similar fashion (e.g., etiologies, pathophysiology, investigations and work up, and management.)

Figure 8:
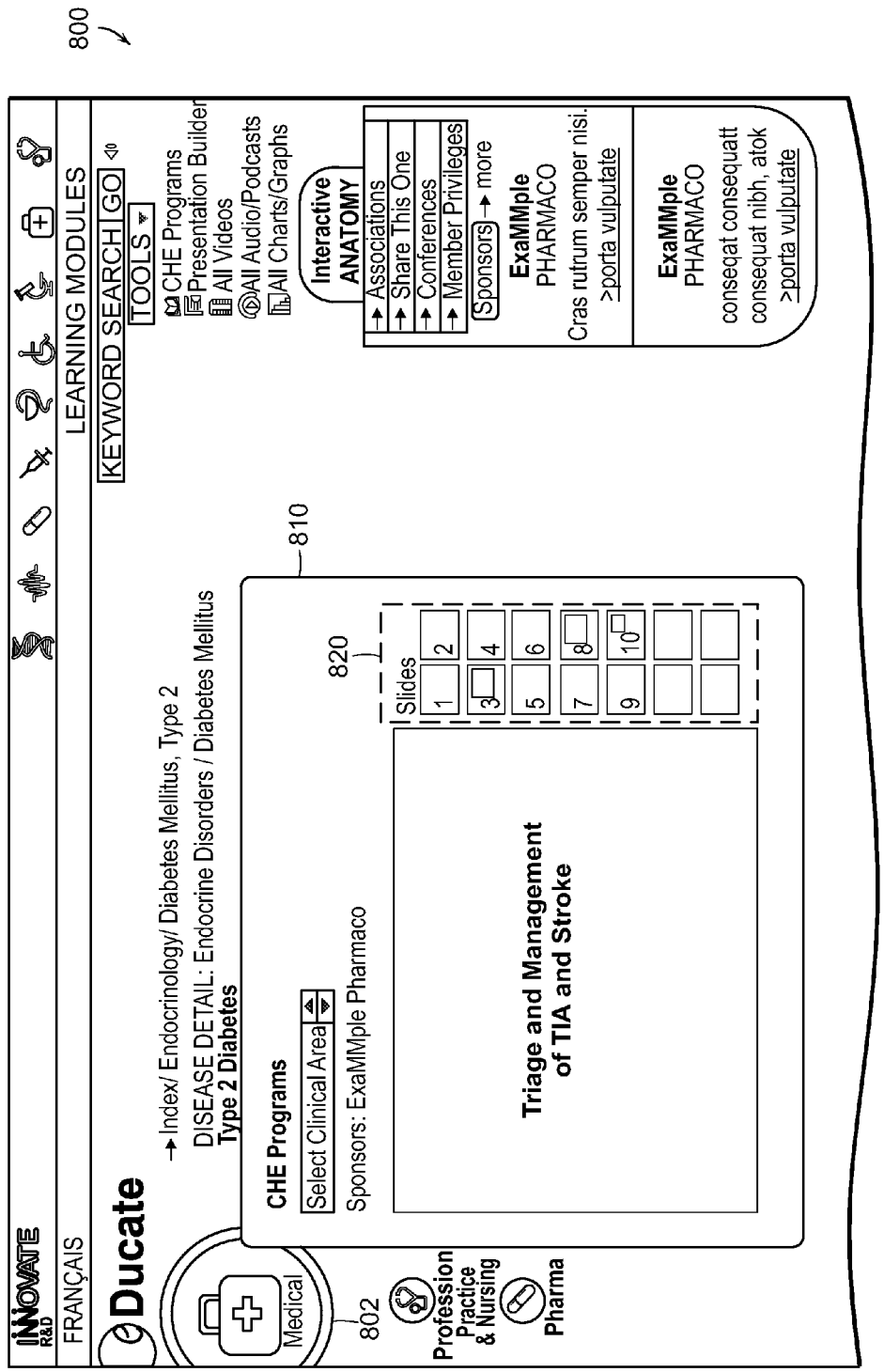
FIG. 8 is an image of an interface page that includes an active CHE Programs sub-page.

As further shown in FIG. 4, the topics page 400 also includes a tools menu 420 identifying one or more computer-implemented tools to perform one or more functions that include, for example, accessing data specific to the selected user (as well as data common to two or more user types), processing the data specific to the selected user type, etc. Amongst the tools that may be invoked from the tools menu 420 is a Continuing health education (CHE) tool that includes programs to present executable programs that have been developed, for example, for a specific disease area. Such programs may have already been developed by third-parties, for example, various pharmaceutical companies or health care organizations (e.g., Canadian Diabetes Association, the American Heart Association, Nursing CHE programs as well as pharmacy CHE programs) that have been imported/downloaded to the local station used by the user, or are executed on remote servers running those programs and sending formatted and/or processed data for display on the interface. The available CHE programs may be implemented for a topic selected from the listing of topic 410 presented on the topics page to present to the user educational materials relating to a selected topic. The Continuing Health Education tool is configured, in some embodiments, to present to the user educational slide show presentations relating to a topic selected from the list 410, or in relation to some other subject matter (e.g., specified via user entered text). With reference to FIG. 8, an interface page 800 is shown that includes an active CHE Programs sub-page 810 on which a PowerPoint presentation for Triage and Management of Transient Ischemic Attacks is presented. The PowerPoint presentation may have been prepared by one or more of the listed sponsors and/or the operator of the system 100, and may have been communicated from a remote data repository. As further shown, on the right hand side of sub-page 810 are thumb-nail representations 820 of the various slides of the particular CHE program being presented in the sub-page 810. In some embodiments, the configuration and content of the page 800 may be based, at least in part, on the selected user type. For example, the specific configuration of the CHE Programs tool shown in FIG. 8, as well as the specific content that can be presented via the CHE Programs tool, may be specific to the selected user type, which in the embodiment shown is a Medical (e.g., physician) user type, as indicated by the icon 802. The Continuing Health Education tool may further be configured to present to the user one or more exams adapted to assess the knowledge of the user and facilitate learning of the subjects presented by the CHE tool. For example, during or after the presentation of some CHE subject, the tool may present a test (e.g., previously prepared as part of the particular CHE presentation) based on the subject presented. Based on the user's score, as determined by the CHE tool, the tool may provide recommendations about any area of weakness that the user should review again and later repeat the test.

Figure 9:
FIG. 9 is an image of an interface page including a Presentation Builder tool.

Another computer-implemented tool is the Presentation Builder configured to enable a user to access data in relation to a particular topic, disease area, or any other information in relation to the one or more subject matters accessible from the interface, and prepare a presentation (e.g., a PowerPoint presentation) for personal or for teaching use. With reference to FIG. 9, an image of an interface page 900 including tools and selectable items to implement a Presentation Builder tool is shown. Presented on the page 900 is a Presentation Builder area 910, defining the working area in which a user can prepare a presentation based on materials made available to the user via the interface 115. Particularly, presented on the area 910 is a current page/slide 920 of the presentation that the user is preparing. The particular slide 920 shown in FIG. 9 is a skeleton (or shell) title slide specifying the various content to be included on the page (e.g., "Module title" information, "Presented by" information, etc.), as well as suggested tentative positions on the slide in which the content to be populated by the user is to appear in the slide. The area 910 also includes a set of navigation buttons 930 to enable selection and other operation vis-à-vis slides of the presentation being prepared. The Presentation Builder page 900 may also include additional buttons and/or other user selectable items to control the content and placement of content within the presentation. In some embodiments, the configuration and content of the Presentation Builder page 900 may be based on the selected user type. For example, the specific configuration shown in FIG. 9, as well as the content that may be presented via the Presentation Builder tool, may be specific to the selected user type, which in the embodiment shown is a Medical (e.g., physician) user type, as indicated by the icon 902.

Figure 10:
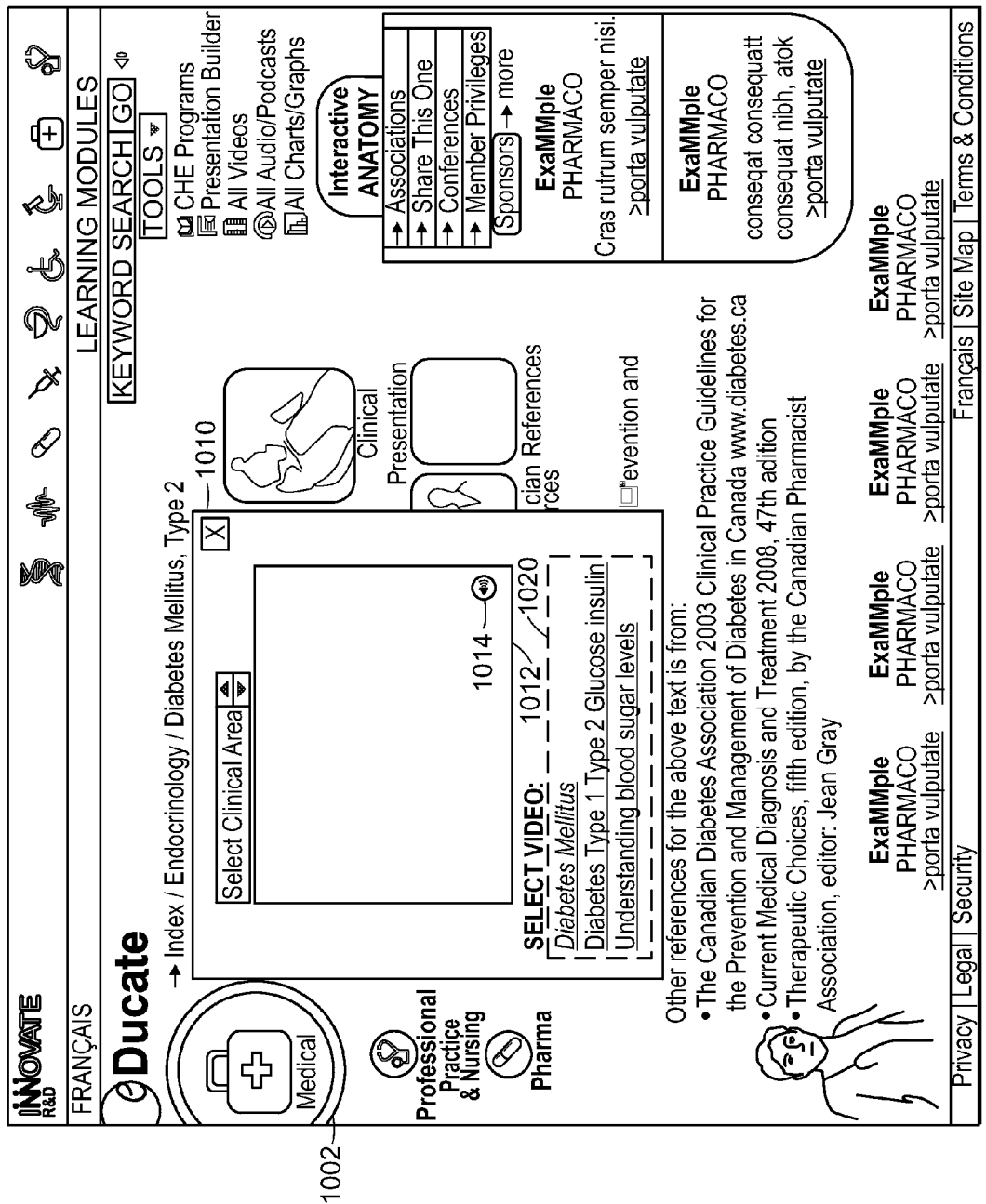
FIG. 10 is an image of an interface page that includes a video player constituting part of an All Video tool.

Another computer-implemented tool available, for example, via the tools menu 420 is an "All Videos" tool where videos on a particular topic, disease/condition area (e.g., insulin resistance or pancreatic dysfunction in diabetes), treatment and therapies (e.g., nursing techniques for drug preparation and administration, or intra-operatives procedures, etc.), and any other subject matter accessible through the interface, is presented. Presentation of content can be done with cartoons, images, live video, etc. With reference to FIG. 10, an image of an interface page 1000 that includes a video player 1010 constituting part of the All Video tool is shown. The video player 1010 includes a control bar 1012 to control such aspects of the video to be played as the volume (e.g., via a user selectable item 1014) and the displayable content. At the bottom part of the video player 1010 are links 1020 to various available videos that the user may play. As with other pages of the interface 115, in some embodiments, the configuration and content of the All Video page 1000 may be based on the selected user type. For example, the specific configuration of the All Video tool shown in FIG. 10, as well as the specific content that can be presented via the All Video tool, may be specific to the selected user type, which in the embodiment shown is a Medical (e.g., physician) user type, as indicated by the icon 1002.

Yet another tool is an Audio and Podcast tool to present audio data relating to, for example, topics selected from the topics list 410. The Audio and Podcasts tool is configured to, for example, present audio presentations by various key opinion leaders in the field of medicine, nursing, pharmacy, any other area of medical care, and/or any other subject matter.

Figure 11:
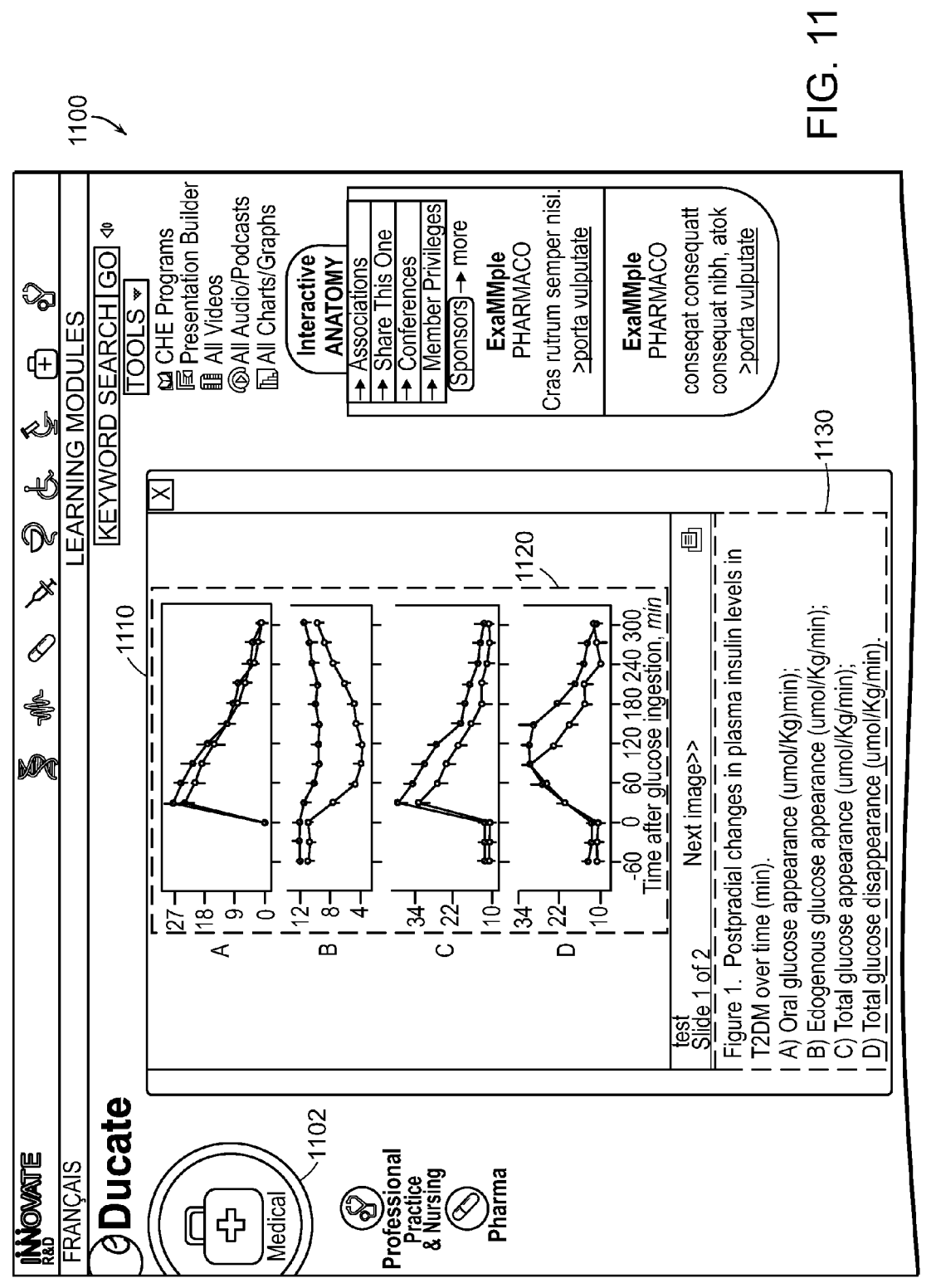

An additional computer-implemented tool that may be included with the tools available through the tools menu 420 is the Charts and Graphs tool to present graphical information relating to, for example, topics selected from the topics list 410. For example, graphical information germane to a particular anatomical system or disease area may be presented, e.g., charts and graphs pertaining to endocrinology or specifically thyroid dysfunction or diabetes. With reference to FIG. 11, an image of an interface page 1100 that includes a Charts and Graphs tool is shown. A Charts and Graphs area 1110 within the page 1100 includes an area for graphical display of information 1120 on which one or more graphs/charts may be displayed. The area 1110 may process contents corresponding to images of pre-processed graphs/charts (i.e., the data from which graphs/charts have been assembled may have been processed at an earlier instance by software implementation associated with the Graphs and Charts tool, or by some other application not necessarily related to the interface 115.) In some embodiments, the Graphs and Charts tool receives raw data corresponding to the graphs and charts to be constructed, and processes the raw data to construct the graphs/charts. Under such circumstances, user-controllers (e.g., a user interface to enable user interaction with the area 1110) to enable control of the formatting and configuration of the graphs may be provided. The area 1110 may also include text-based information area 1130 on which alpha-numerical content, e.g., content pertaining to the graphs/charts being displayed, is provided. As with other pages of the interface 115, in some embodiments, the configuration and content of the page 1100 may be based, at least in part, on the selected user type. For example, the specific configuration of the Charts and Graphs tool shown in FIG. 11, as well as the specific content that can be presented via the Charts and Graphs tool, may be specific to the selected user type, which in the embodiment shown is a Medical (e.g., physician) user type, as indicated by the icon 1102.

Figure 5:
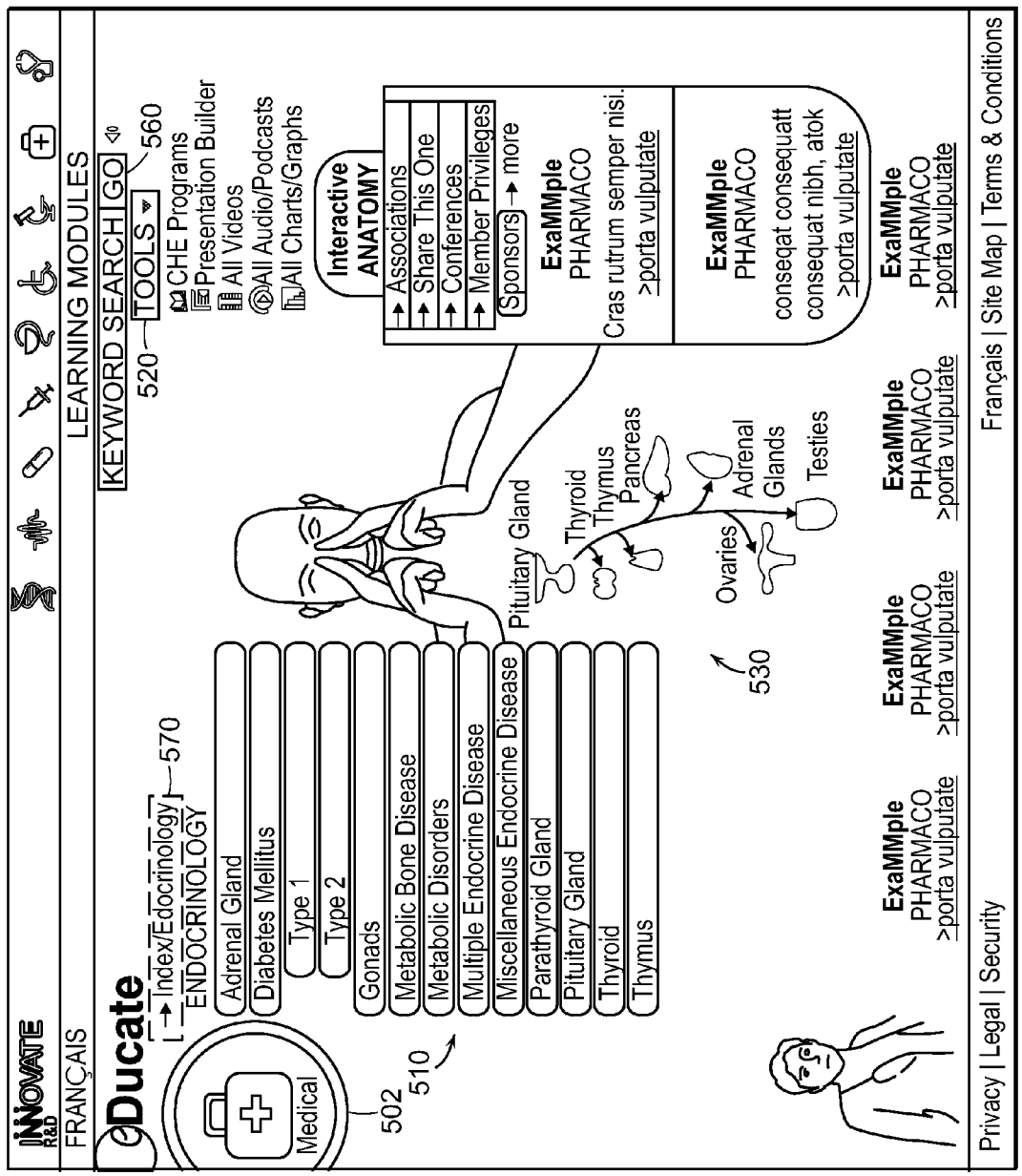
FIG. 5 is an image of a sub-topic page.
Figure 12:
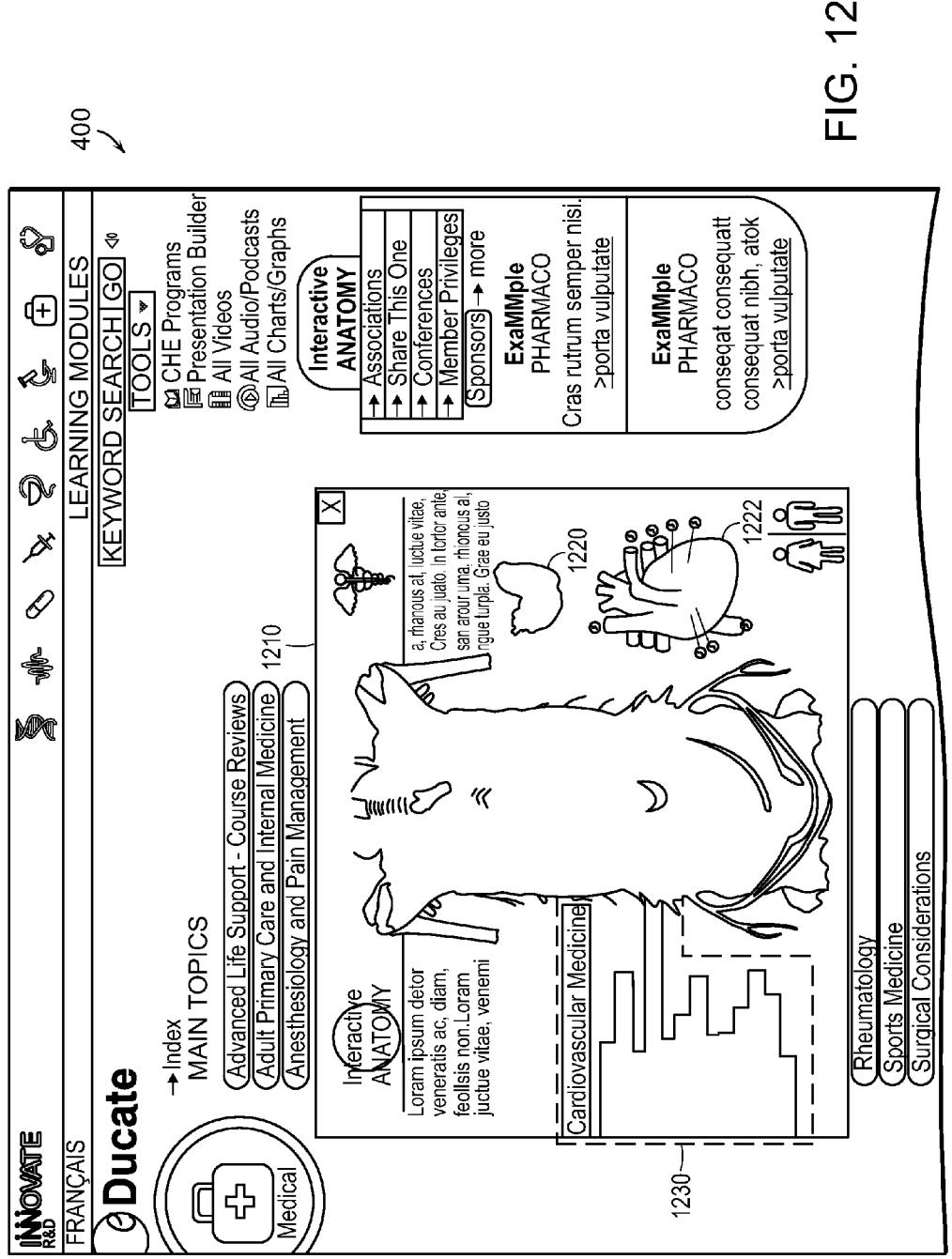
FIG. 12 is an image of a page that includes an activated interactive model of skin and muscle layers peeled away to reveal internal organs.

With continued reference to FIG. 4, in some embodiments at least some of the screens/pages presented by the interface include an interactive anatomy tool 430, positioned in the topics page 400 to the rights of the topics list 410. The interactive tool, when activated, includes a model relevant to the one or more subject matters with respect to which the system 100 is presenting data. The interactive model 430 may be activated, for example, by clicking on a position within the model 430, or by clicking on the user selectable icon 432 marked "Interactive Anatomy." The configuration and layout of the model presented may depend, in some implementations, on the user-type selected. Thus, when presenting medical/health care information, a physician may be presented with a more elaborate interactive anatomical model than the model that would be presented to some other health care practitioner whose requirements for information provided through this type of model are different. As further shown in FIG. 4, as well as in FIG. 5, showing a specific topic page 500 drilled-down from the topics page 400 by the selection of one of the topics (in this case, the topic pertaining to Endocrinology), the interactive anatomical tool 430 is implemented as a composite of graphical layers that are each representative of different anatomical structures of the human body. At least one of those composite layers can be interactively displayed or suppressed so that if the user wishes to focus in on a particular anatomical system, the user can interactively select the layer associated with that system, which would then be activated and be displayed more prominently than other layers constituting the model. For example, other layers not selected could be presented in a faint or fading format to highlight the selected layer. Additionally and/or alternatively, one or more layers may be entirely suppressed to thus leave the remaining layers (or a remaining single layer containing the details that the user wishes to study more carefully) as the only visible layers. An example of an interactive model activated by clicking on the model 430 or by selecting the user selectable item 432 is shown in FIG. 12. The page shown (which may be the page 400 or some other page) includes an embodiment of a model 1210 of skin and muscle layers peeled away to reveal the internal organs of the thorax and abdomen. The user is free to select which system he/she would like to further explore. In this example the user hovers over the heart to thereby trigger: (i) two anatomical illustrations 1220 and 1222 of the heart to the right of the main body, and (ii) an area 1230, on the left side of the activated model 1210, containing a series of cardiac conditions. The user may then continue to either further explore the anatomical structures and normal cardiac physiology by clicking on the displays of the heart to the right (the illustrations 1220 and/or 1222) or can obtain more information pertaining to any of the cardiac conditions listed in the area 1230. Selection of any of the clinical conditions to the left, for example cardiomyopathy, may cause (i) a change in the image displayed to show pathology, for example, of an enlarged heart that is observed with cardiomyopathy, and (ii) associated text describing the anatomical, etiological, pathophysiological and clinical changes associated with cardiomyopathy.

Figure 6:
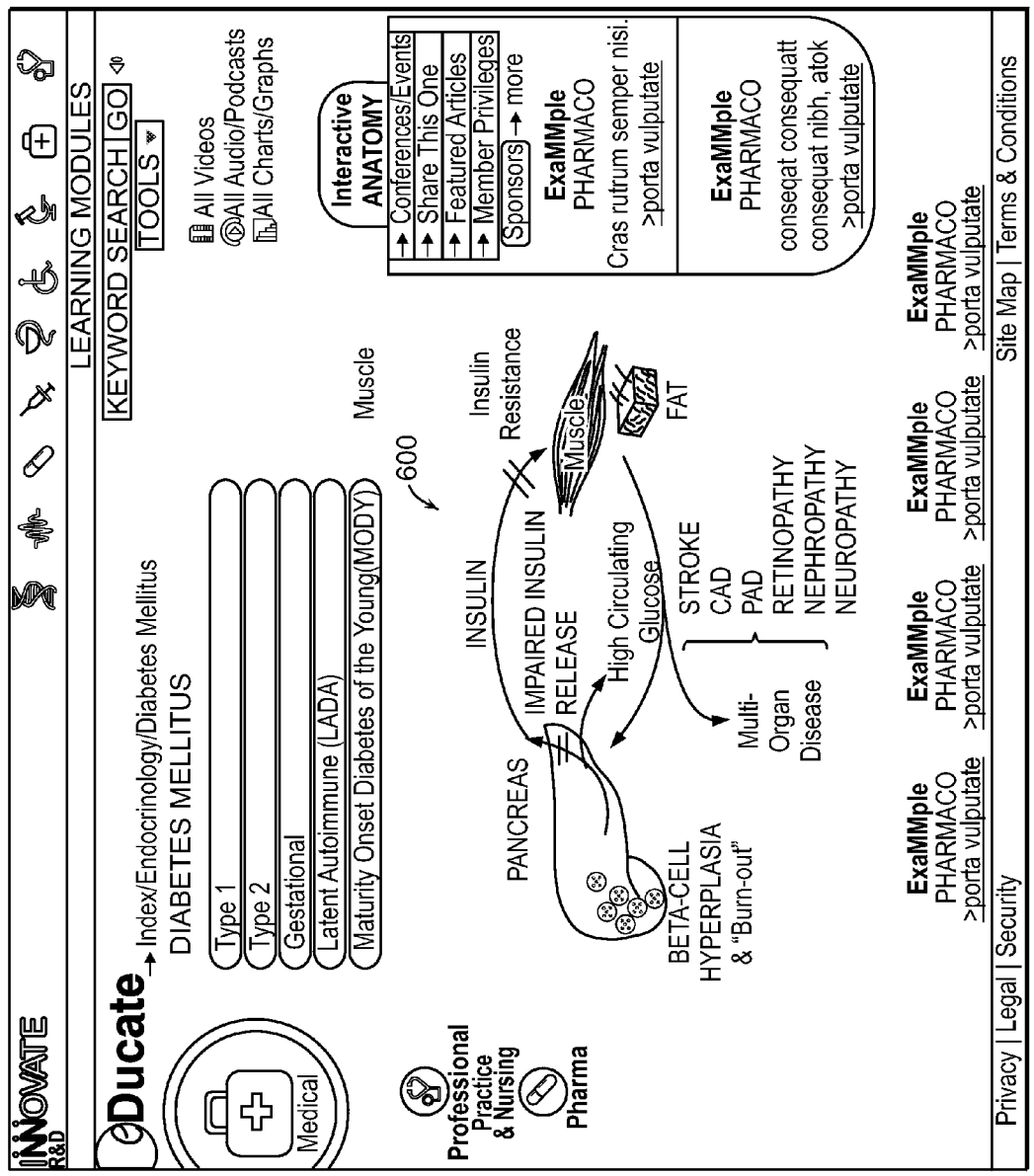
FIG. 6 is an image of a disease topics sub-page.

The interactive tool 430 may be configured to display an interactive physiology and/or an interactive pathophysiology model. In other learning arenas the interactive section may be used to display interactive material (models, graphs, flow charts, methods etc) that would assist learning. In operation of the tool 430, clicking the interactive anatomy area would give rise to various anatomical displays depending, at least in part, on a disease area that a user may be interested in. For example, as shown in FIG. 6, and as will become apparent below, as the user drills-down to a page providing more specific data on a disease, such as diabetes, the diabetes interactive anatomy model may show a human body or organs displaying the key sites of dysfunction in the disease process. For example, in the diabetes module 600, the pancreas, muscles, and fat tissue may be displayed, as well as the normal interaction between insulin and its target tissues. The model may also display the pathophysiology of the disease, e.g., improper production of insulin or insulin resistance at the peripheral tissues including muscle and fat. By selecting one or more positions on the interactive anatomical model, additional medical data corresponding to the selected one or more positions may be displayed.

Another type of an interactive model is an assimilation model that includes graphical data pertaining, for example, to at least one topic selected from the listing of topics relating to the one or more subject matters. An assimilation model is generally a reverse concept of the "peel away" anatomical model. The assimilation model begins at the level of the cell and assimilates upwards through the organ level, the system level, and the body level. e.g., starting from a representation of beta cells, an assimilation model may be configured to present a layer corresponding to beta cells, followed by a pancreas layer, an endocrine layer and a body layer. An example of a type of an assimilation model is the molecular assimilation model which may include a composite layer interactive graphical molecular model depicting the interaction of substances with one or more cells and/or with organs in the human body. An assimilation model may enable a user to view how and where drug or disease (e.g., viruses) interactions take place at the level of the cell, and expand the details of the interaction through the organs, showing, for example, the sites of drug metabolism, the main benefits of the administered drugs, and sites where potential side effects may be manifested, etc. For example, the chemotherapeutic drug Adriamycin is thought to work through its ability to bind to DNA and inhibit nucleic acid synthesis, in the process killing cancer cells but at the same time being toxic to heart muscle, which can thus lead to heart failure. Accordingly, the assimilation model presenting the interaction and effect of Adriamycin at various levels provides a view of the molecular events of drug and disease actions within the cell, organs (including benefits and adverse events/effects) and the body (including the benefits and adverse effects, e.g., heart failure, sequelae, etc.)

As noted, on the topics page 400, the model 430, presented for health care subject matters implementations as a ghosted human body, will be interactive, e.g., hovering over the patient's eyes or brain will open modules on ophthalmology or neurology/neurosurgery, respectively. As noted, the body model will also have "peel away" functionality (e.g., when activated) so that the user can drill through various levels of the human anatomy into specific symptoms (as shown, for example, in FIGS. 4, 5 and 12). For example it would enable moving from skin representation into the muscular system, displaying anatomy and linking to physiology and muscle diseases. It would also allow a drill through functionality beyond muscles into the skeletal system, providing the major anatomy, physiology, and pathophysiology (diseases) that are associated with bones. Other systems including the digestive tract, the respiratory system, cardiovascular/vascular system, nervous system, and endocrine system, etc., could also be included. In short, any system involved in human anatomy, physiology, and disease may be covered.

In some embodiments, the interface enables display of various associations related to a particular topic, disease, or some other subject matter selectable by the user. For example, depending on a disease selected by the user to obtain further information, one or more pages presented on the interface, including the topics page 400, could display emblems and/or hyper links to such associations as the American Heart Association, American Diabetes Association, Canadian Heart and Stroke Foundation, etc.

As further shown in FIG. 4, the topics page 400 includes a user selectable item designated as a "Share this On:" link 440. The link 440 is a link to the major internet networking sites including, but not restricted to, regular email, MSN messenger, Facebook, Digg It, Stumble upon it, Newsvine, Twitter, Delicious, etc., and may also enable the incorporation of new communication tools as they become available. Thus, a user, upon viewing data that the user wishes to share with one or more other users, may select the "Share This On:" link to reveal a list of one or more communication applications such as those listed above. In response to selection of one of those applications, the selected application becomes active, enabling the user to add a comment to be communicated to the intended recipients, attach some or all of the information being presented on the interface 115, or otherwise perform other functions to communicate with other users. Upon completion of the user operations on the one or more selected applications, the content of the communications is forwarded to the intended recipients. The tool may be accessible from other pages.

Yet another tool accessible from the topics page 400 is the Conferences/Events tool 450 which, in response to selection of that tool, provides information about upcoming conferences and events in a specific area and in relation to the one or more subject matters with respect to which the user is obtaining information. In some embodiments, an eCalendar (not shown) may be included within the tool to provide reminders to the user regarding upcoming conferences, meetings and examinations, as well as day-to-day activities, if required. The calendar may be personalized, and the user may manually enter any information directly onto the calendar or can select automatic updates from any given healthcare field that would automatically update the calendar with the required information. The calendar will enable selection of updates from a drop down menu that will cover examination schedules from various examining bodies (medical, nursing, pharmacists etc.), as well as upcoming meetings/conferences within, for example, a specific disease area. The tool 450 may be accessible from other pages and provide progressively narrower information from those other pages as the user drills-down to more specific topics and sub-topics from the topics page 400. For example, if the user is within the neurology module, the user would be able to see upcoming conferences and examinations relating to that topic, such as meetings of the American Neurological Association, the Canadian Neurological Sciences Federation, upcoming National or international meetings in relation to Parkinson's disease, American Board of Psychiatry and Neurology Examinations schedules, etc.

A further tool available from the Topic page 400 (as well as from other pages) is the Member Privileges tool 460. The tool 460 enables the user to access information on special membership programs, offers or benefits provided by any of sponsors and partners that place marketing materials and advertisement on the information presentation management system 100. The members' privileges accessible by the user through that tool may include special promotions for hotels, travel, rental cars, loyalty points, luxury brands, etc.

Also presented on the page 400 (and/or on other pages) are sponsors' display and sub-pages 470. The display 470 includes, in some embodiments, the display of sponsors/advertisers, such as pharmaceutical companies who use the interface to access and promote their products to health professionals. Other types of sponsors/advertiser who may include promotional materials on the pages of the system 100 include medical supplies companies, universities, colleges, health care associations (e.g., American or Canadian Diabetic Association), etc. In some embodiments, the selectable item for sponsors may appear at the bottom of the interface page, as shown, for example, in FIG. 3B and in FIG. 14 (more particularly described below).

In some implementations, the content displayed by some of the sponsors is configured as a user selectable item (e.g., a hyperlink activated by clicking in the area occupied by the marketing content of the sponsor, such as the sponsor's logo) that, upon selection by the user, leads the user to a separate sponsor page that may have been co-developed by that sponsor (e.g., a specific pharmaceutical company) based, at least in part, on formatting and content guidelines compatible with the system 100 and the interface 115 (e.g., guidelines provided by the eDucate platform). For example, clicking on the ExaMMple Pharmaco icon would open up a page that would enable the user to access information about the company and their therapeutic areas, as well as some other data germane to the user's practice such as clinical trials data, pipeline agents, CHE programs that may be available from that sponsor, etc. The sponsor sub-page may enable incorporation of other materials into the page(s).

Figure 13:
FIG. 13 is an image of a sponsor's page.

With reference to FIG. 13, an image of a sponsor's page 1300 is shown. The sponsor's page 1300 may include a tools section, similar to the tools menu 420 of the page 400, a "conferences and events" tool, listing, for example, the conferences and events that the particular sponsor may be involved with locally, regionally, nationally, or internationally, as well as other tools. Sub-pages of non-pharmaceutical companies may include data and tools similar to data and tools presented on pharmaceutical companies' sub-pages. Other configurations and presentation formats for the sponsors page may be implemented and used.

In response to selection of one of topic identified in the topics listing 410 of the topics page 400, the system 100 retrieves and presents a listing of sub-topics related to the selected topic. With reference to FIG. 5, an image of a sub-topic page 500, also referred to as topic selection page, is shown. As with some of the other pages presented on the interface 115 of the system 100, at least some of the information presented may be based on the selected user-type. As shown in FIG. 5, the icon 502 captioned "Medical", corresponding to physician user-type, is the active user icon, indicating that information specific to this user-type is presented on the current page. The page may also present information that is common to two or more (or even all) the user types that may be using the system 100. In the particular example depicted in FIG. 5, a listing 510 of endocrine disorders, including adrenal glands diseases, diabetes, gonads diseases, metabolic bone diseases etc., is presented in response to the user's selection of the Endocrinology topic 414 from the topics listing 410 shown in FIG. 4. The selection of a topic from the topics page thus causes the presentation of a sub-page to categorize the disease and disorder topics within that area. As further shown in FIG. 5, the sub-topic page 500 includes at least some of the tools and features that were also available on the topics page 400, including the presentation processing tools, the interactive model tool, a listing of sponsors/advertisers, etc. In some embodiments, the content presented or processed by the tools is adjusted to reflect the more specific topic that was selected by the user. Thus, for example, having selected the Endocrinology topic from the topics page 400, the content presented on the interactive anatomical model 430 is adjusted to present content germane to endocrine system. Specifically, an interactive diagram flow 530 of the endocrine system, including the various glands and pathways, that enables display of the anatomy, physiology, pathophysiology and drug interaction by those organs, is illustrated. In some embodiments, the user can obtain further information about the system by positioning a cursor over one or more positions on the model 530.

The endocrine system depicted on the interactive model 530 (the ghosted human model), and also available through the interactive anatomy, enables an interaction by, for example, hovering over a particular area to open the anatomy, physiology and/or disease associated with that specific area. For example, hovering over the pancreas allows the interactive anatomy and/or interactive physiology components to become available for pancreatic structure and physiology, and also allows organ-specific diseases to be displayed in text. Some of the displayed information is presented as a user-selectable item (e.g., hyperlinks, icons, etc., that can be invoked to launch another application or page) such that selecting any of the items will enable, for example, opening a sub-page specific to that disease. For example, diseases such as pancreatitis, pancreatic cancer, and diseases associated with the pancreas may be displayed (not shown in FIG. 5) and clicking on one of the diseases will allow a drill down into pages or links corresponding to, for example, diabetes type I and/or type II.

As further noted, available from the sub-topics page 500 (in this case, the endocrinology page) is a tools menu 520 similar to the tools menu 420 available from the page 400. Amongst the tools that can be selected from the menu 520 are the continuing health education (CHE) programs tool (see also FIG. 8), the Presentation Builder tool (see also FIG. 9), the All Videos tool (see also FIG. 10), the Audio podcasts tool, and the Charts and Graphs tool (see also FIG. 11). The Interactive Anatomy, Associations, "Share this on", conferences/events and member privileges tools are also available from the sub-topics page 500, as are the pharmaceutical sponsors' information, Medical Supply companies' information, etc. As also noted, in some implementations, selection of any of the tools, content and/or links will cause the presentation of resultant content (by presenting content on the page 500, opening sub-pages, etc.) germane to the topic or sub-topic selected and/or based on the specific user-type selected by the user.

Further available from the sub-topics page 500 (as well as from other pages, including, for example, the topics page 400) is a Keyword Search tool 560, displayed at the top right hand corner of the page. The sub-topics page 500 also includes a "breadcrumbs" feature (sometimes referred to as a cookies application) that enables the user to determine which page it is viewing relative to the root or parent page, and thus enables the user to easily retrace its steps. In this case, the breadcrumbs feature 570 shows the path the user has taken includes the index page (the topics page 400) and the endocrinology sub-topic page 500.

Figure 7B:
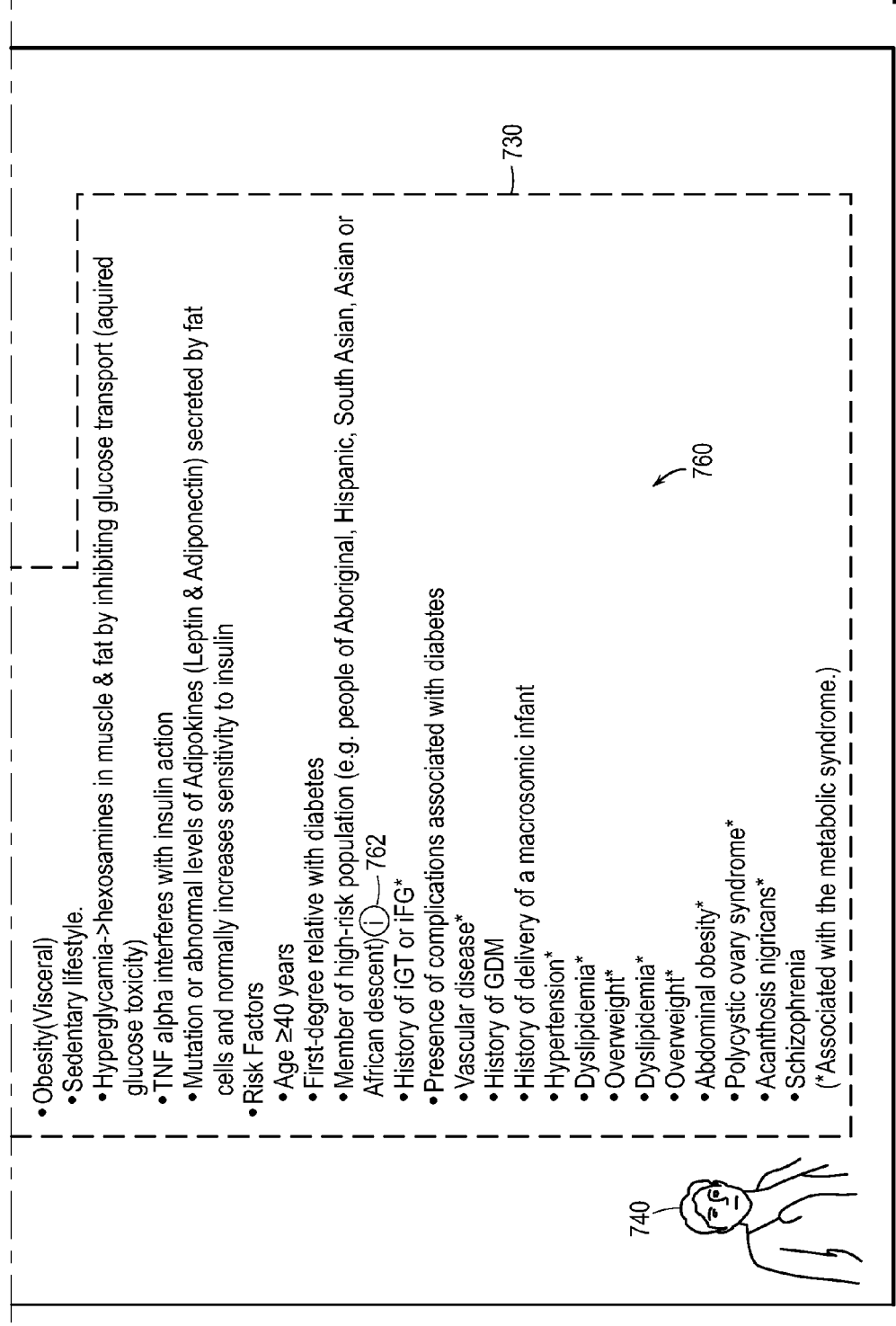
FIG. 7 is an image of a disease detail page that includes information about a disease.

In response to selection of one of the sub-topics from the sub-topics list 510, selection of one of the diseases presented on page 600 of FIG. 6, selection of a topic from the topics list 410 and/or a selection of a selectable item from the interactive anatomical models (such as the model 530), a disease detail page 700, an embodiment of which is shown in FIG. 7, is presented that includes information about the disease with respect to which the user wishes to obtain more information. In the example depicted in FIG. 7, the specific disease presented is type II diabetes.

In some implementation, a user may be directed from a landing page, such as, the landing page shown in FIG. 3A (or the landing pages of FIG. 3B or 14) to the more specific information (e.g., disease information, where the subject matter being presented is health care information) shown, for example, in FIG. 7, without having to navigate through multiple drill-down pages such as the pages depicted in FIGS. 4, 5 and/or 6. Instead, the landing page may be configured so that upon selection of one of several practitioner types, one or more levels of sub-menus are presented (rendered) on the same page where the list of topics was presented.

Thus, in such implementations, the main landing page may contains key components of the configuration of the example landing page 300 (as depicted in FIG. 3A), but reorganized so that, for example, the user selectable items identifying the user types (e.g., practitioner types) are on the left-hand side of the page. Such a configuration enables displaying the components/constituents of, for example, the topics page (providing health-related categories such as various physiological/anatomical systems, in situations where the subject matter being presented by the system 100 is that of health care). A landing page with this alternative configuration also enables presentation of "drill-through" ("drill-down") functionality similar to that provided by the example interface drill-down pages shown in FIGS. 5 and 6. For example, in some embodiments, selection of topics, sub-topics, etc., may be performed by hovering over the user type, which in turn causes a topics menu (including selectable topics similar to those presented in FIG. 4) to be presented, and continuing to select a path by hovering over desired topics, sub-topics, etc. Embodiments of such an alternative implementation of the landing page can therefore eliminate 2-3 clicks, thus creating a 1-click system that enables navigation to the main detail page (e.g., a disease detail page, such as the one shown in FIG. 7.

Figure 14:
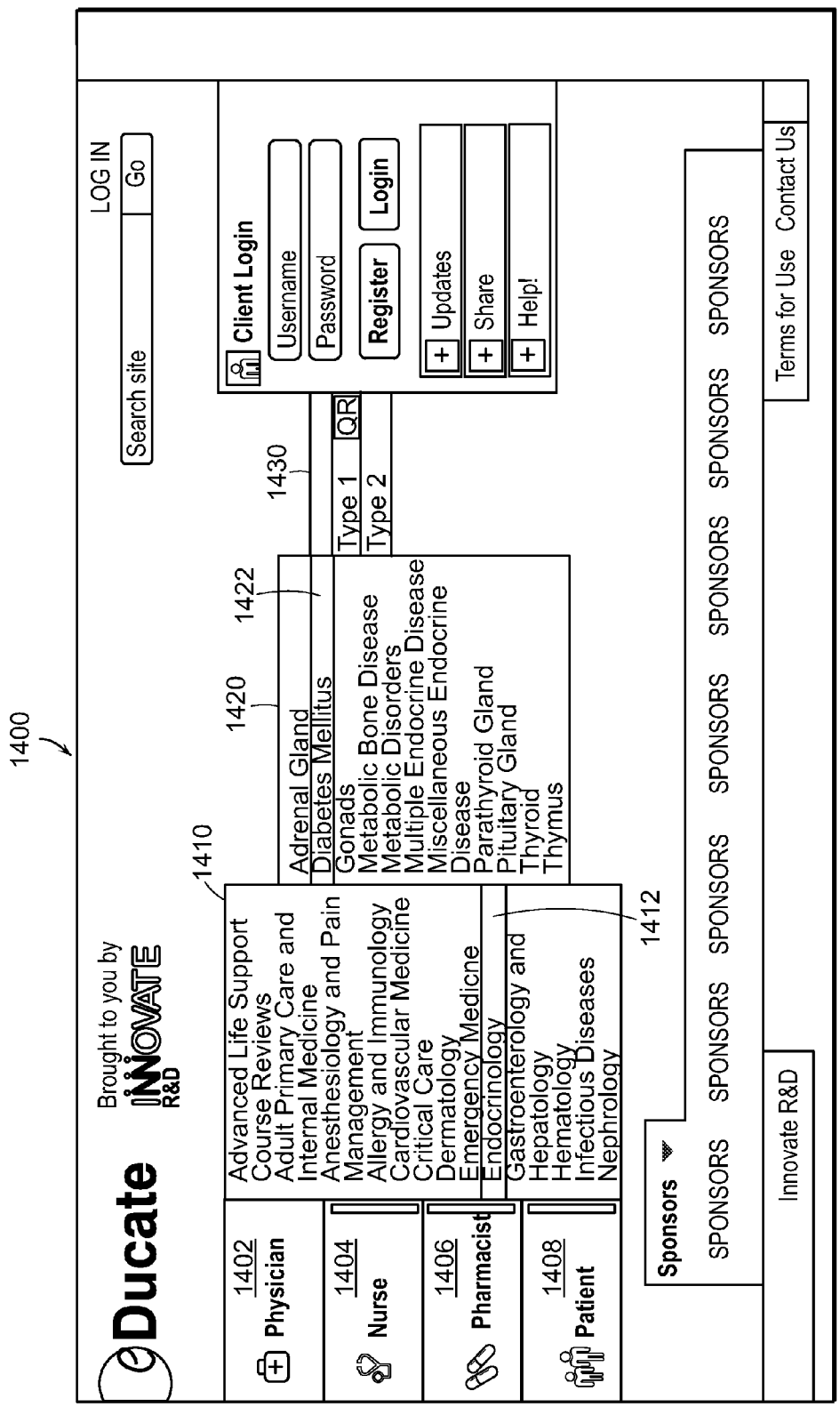
FIG. 14 is an image of another example landing page configured to present drill-down sub-menus on the same page.

Thus, and with reference to FIG. 14, an implementation of another example landing page 1400 (which may be similar to the landing page 350 of FIG. 3B) configured to present drill-down sub-menus on the same page to enable a quick selection of desired information, is shown. Similar to the example landing page 300 of FIG. 3A, the landing page 1400 includes selectable items 1402, 1404, 1406, and 1408, to enable selection of one of various practitioner-type users (e.g., a doctor, a nurse, a pharmacist), and also a non-practitioner user type (in this case, a patient). Upon selection of one of the user types (e.g., one of the practitioner types), a listing of topics, in this case relating to the subject matter of health care, is presented (rendered) on the landing page interface. The listing of topics may be presented as a menu extending from the selected user type selectable items. Thus, in the example depicted in FIG. 14, in response to selection of the physician user type, e.g., by hovering over the selectable item 1402, a menu 1410 of topics associated with that user type for the particular subject matter (which may include topics that are specific to that type and/or topics that may be common to multiple user types) is presented.

Subsequently, the user may continue to drill down by causing additional levels of drill-down sub-menus to be presented in response to further selections from preceding levels of sub-menus. Thus, in the example of FIG. 14, upon selection of selectable item 1412, corresponding to the topic of endocrinology, a lower level drill down sub-menu, in this case sub menu 1420 is presented in the landing page 1400, to list, in this example, diseases associated with the topic selected from the preceding sub-menu level, namely, the list of topics from sub-menu 1410 that was selected for the physician user type. If there are additional levels of sub-menus that can be presented to provide even more specific sub-topic in relation to which information is to be provided to the user, such additional levels of sub-menu may also be presented by selecting one of the items in the last sub-menu to be presented/invoked. In the example of FIG. 14, in response to selection from the sub-menu 1420 of item 1422, corresponding to the disease of diabetes mellitus, a further lower-level sub-menu 1430, is invoked, to list disease types (e.g., Type 1, Type 2) associated with the selected disease from the preceding sub-menu level. As shown in FIG. 14, the presented sequence of sub-menus can be presented so that a sub-menu is connected to and extends from a preceding sub-menu level.

Thus, in some embodiments, in response to selection of one of user selectable items identifying the at least one of the two or more practitioner types, a menu including a listing of topics relating to one or more subject matters (e.g., health care) is presented. When a selectable topic from the list is associates with one or more drill-down levels of sub-menus of sub-topics relating to the selectable topic, one of the one or more drill-down levels may be presented by selection of an item from a sub-menu of a preceding drill-down level associated with the topic selected from the listing of topics and with the one of the one or more drill-down levels of sub-menus. In some implementations, the listing of topics includes a listing of health care topics, and, in those situations, presenting the one of the one or more drill-down sub-menus includes a list of diseases associated with the selected topic, returning to FIG. 7, to facilitate learning. The format by which information is presented is standardized such that the various user types (e.g., in circumstances where the system 100 is used to present information relating to health care, the user types are health care practitioners) are exposed to the same key information and would be able to share the same base information for better understanding of the disease process and use of medications. Thus, selecting a specific disease (e.g., type II diabetes) results in the opening of a disease specific page, in this case the page 700. The disease page (or some other specific subject drilled down from a topics page corresponding to the subject matter with respect to which information is to be presented) is presented as a standardized set of information in a succinct, clear format that covers pertinent information relevant to the user types (e.g., health care professionals).

More specifically, for the selected user-type (e.g., a doctor user-type selected from a plurality of health professionals user types), the user-type specific information is arranged using a standardized presentation format to facilitate accessing the presented information using a set of pre-defined user-selectable items. For example, disease pages, such as the type II diabetes page 700, include specific icons that deal directly with health care professional information and resources and making it available to all users to seamlessly navigate through a large body of information and allow access and download of "resource tools" through an educational portal/forum such as the portal described herein. Icon consistency engenders familiarity and keeps key information consistent among all health care groups. This concept of engaging similar yet distinct user groups through the use of such user selectable items (icons) arrangement is unique to the implementations described herein.

As described herein, in one or more of the pages, one or more data sets of the retrieved information (retrieved from one or more local and/or remote repositories) that are presented include information specific to the selected user type, while one or more other data sets include information that is common to two or more user-types. Thus, the disease detail page 700 enables accessing and/or presenting information that is common to several health care professionals. For example, the top icons 710 reveal five key areas pertinent to physicians, nurses, and pharmacists. Those key areas of information may include, (i) definition of the disease or condition, (ii) epidemiology, (iii) pathophysiology, (iv) etiology, and (v) clinical presentation. These icons may remain the same regardless of the disease or topic selected from preceding pages of the interface/portal, thus engendering familiarity with a specific icon and the understanding of what the icon means so as to enhance usability and navigation, and shorten the typical learning curve.

While the initial set of user selectable items (e.g., five icons) common to two or more user types provides the two or more user types (and, in some circumstances, all the user types) with a constant information core, a second set 720 of user selectable items (e.g., the icons located in the row below the set 710) is generally individualized based on the user type selected by the user. Thus, in the disease detail page 700, the interface/portal is configured to present a first area that includes user selectable items common to the two or more user types, and to present a second area including user selectable items specific to the selected user type.

In the example of FIG. 7 in which the interface presents health care information for health care professionals, and the selected user type is that of physicians (as indicated by the active Medical icon 702), the user selectable items 720 include selectable icons (e.g., icons associated with computer-implemented tools), for: 1) differential diagnosis, 2) investigation and work up, 3) treatment and guidelines, 4) randomized clinical trial, 5) pipeline agents, 6) physician resources, and 7) references. Selection of one of the physician-specific user-type icons would cause physician-specific information relating to type II diabetes (or whichever topic/sub-topic was previously selected) to be presented. For example, in response to a selection of the physician resource tool, a sub-list of tools that may include, for example, a disease management flow chart and a decision making tool, enabling the user to activate one of those tools and/or obtain further data in relation to those tools.

Had a different user-type selection been made, individualized selectable items specific for that user type would have been presented to enable presenting information specific for that user type. For example, for a nursing user-type, nursing-specific icons (associated, for example, with computer-implemented tools) may include: 1) a nursing treatment goals tool, 2) a nursing differential diagnosis and intervention tool, 3) a medication tool, 4) a complications tool, 5) a health teaching tool, 6) a nursing resources tool and 7) a references tool. For a pharmacist user-type, the set of pharmacist-specific icons (which may be associated, for example, with computer-implemented tools) may include, 1) a clinical outcome tool, which provides information on what is the anticipated outcome from pharmacologic intervention (e.g., in a hypertension module the outcome information to be provided with respect to the operation of initiating antihypertensive therapy would be (i) reduction of blood pressure but also (ii) less risk of atherosclerosis, (iii) Heart disease and (iv) stroke), 2) a treatment and guidelines tool to provide data regarding treatments and guidelines for the selected disease, 3) a medication tool, 4) a randomize clinical trial tool, providing information on whether a drug has been determined useful or not, and generally including presentation of the most rigorous trial data in a particular field, e.g., trial data that will impact most on medical/pharmacological practice, 5) a pipeline agent associate with a tool to provide data on new and emerging therapies within a disease area, 6) a pharmacists resources tool, and 7) a references tool.

As further shown in FIG. 7, the page 700 includes a third area 730 where data relating to the selected disease (or other topic drilled-down from a parent page for some other subject matter) is presented in response to a selection of one of the user selectable items in the sets 710 or 720. For example, in FIG. 7, in response to a selection of a physician resource tool 722, and the subsequent selection of medical management tool (not shown), data pertaining to medical management for diabetes mellitus is presented. The third area may also include an interactive model similar to the models 430 and 530 shown respectively in FIGS. 4 and 5.

In some embodiments, a user who selected a particular user type and consequently been presented with at least some information corresponding to that user type may change its user-type selection to select a different user type and thus have access to information and tools associated with that newly selected user type. For example, a user who selected a Medical (physician) user type and thus has been presented with physician-specific tools and data accessible from the icon set 720 may select a different user type, e.g., nurse, by clicking on the professional practice icon 704 on the left hand side of page 700. Selection of the professional practice user-type would cause a new set of user selectable items corresponding to that user-type selection to be presented in place of the user selectable items associated with a physician user-type. On the other hand, the top five icons in the set 710 may remain the same as those are the icons associated with tools/data common to two or more user-types.

For each of the specific user-type resources, e.g., for physicians, nurses, and pharmacists, specific information will be provided to enhance the health care professional-patient interaction. For example, as noted, for a physician user-type, the resources available to the user may include a disease management flow chart, dietary guidelines (if appropriate), assessment tools such as understanding the Framingham scoring system for cardiovascular disease, or a stroke triage tool to allow the user to understand the urgency in treating acute stroke, transient ischemic attack, etc. Physical examination forms and patient medication handouts and patient diaries could also be part of the physician resources. Resources and data specific to nurses and pharmacists user-types may include patient education handouts, patient diaries, assessment tools that would be specific to nursing or pharmacists, and disease management flow charts catered for nurses and pharmacists.

In some embodiments, the information presentation management system includes presentation of information and enhanced learning in relation to drug/medication utility, including drug use, dosing, mechanisms of action, drug delivery and metabolism, adverse effects, contraindications and interaction, i.e. drug information, through interactive picture-graphical, cartoon, and/or video display. This information may be retrieved in response to selection of the treatment and guidelines icon. From there, additional interactive icons may be presented to enable launching of videos (e.g., animated videos, or filmed videos), which may also be accessible through the "All videos" icon on the page. Hovering or clicking on a given drug or specific aspect relating to the drug (e.g., adverse effects) will link the interface to data that includes videos, cartoons or real life displays. The latter can be used to show, for example, (i) drug and pharmaceutical benefits (e.g., video display of a Parkinson's patient before and after use of an anti-Parkinson medication), and (ii) CT scan of a brain hemorrhage that might occur as a side effect of "clot busting (tPA)" agent used to treat acute stroke patients. In some embodiments, the interactive "peel away" model of the human body used to present anatomy, physiology and pathophysiology information (as shown, for example, in FIG. 12), may be adapted to present information regarding drug use and delivery showing the main points of interaction within the body. Such a model could be implemented to peel away to specific organs, sub-structures within the organs, cellular and molecular levels layers in the organs. An "assimilation" model can also be used, e.g., presentation of composite layers beginning at the molecular level and working upwards (e.g., molecular→cellular→organ→body).

As noted, in some implementations of the interface, the page 700 includes a first area with one or more user selectable items common to two or more user types and a second area with one or more user selectable items specific to a selected user type. The page 700's third area is also referred to as a "whiteboard" (or "eWhiteboard") in which information (text, images, video, audio, etc.) is presented in response to selection of one of the user selectable items (e.g., icons). For example, clicking one of the icons in the first and second areas results in dropdown 760 of information into, in some embodiments, a clear pallet in "bullet" format for easy reading, and information gathering and learning.

The page 700 also includes a tools menu 780 that may be similar to the tools menus appearing in pages 400 and 500. Computer-implemented applications that can be selected and invoked from the tools menu include CHE programs, a Presentation Builder, an All Videos tool, an All audios and Podcasts too, and a Graphs and Charts tool. For example, the Presentation Builder can be used here by clicking on any of the icons shown to enable the system to facilitate building a PowerPoint presentation for the user. Clicking on definition, epidemiology, and etiology, as well as randomized clinical trials would allow a series of slides to automatically be built from the data that is managed and presented by the system.

The page 700 may further include a sponsors page, an interactive anatomy/physiology/pathophysiology model tool, an Associations feature, a "Share this on:" tool, and a Member Privileges feature that are similar to the respective tools described in relation to pages 400 and 500 depicted in FIGS. 4 and 5, respectively. Also shown in FIG. 7 is the breadcrumbs feature 790, which is similar to the breadcrumb feature 570 described in relation to FIG. 5, presenting the drilled-down path from the system's index through endocrinology and ending at the specific disease of diabetes type II.

In some embodiments, the interface of the system is configured to cause magnification and "bubbling" of an image of an icon when hovering over the icon with a mouse (i.e., causing the icon to be enlarged into a slightly lager image when hovering over the icon, thus creating the effect of the icon being blown up into a bubble.)

In some implementations, the system may be configured to provide interactive information within the main text. Specifically, throughout the text there will be sections for which a user can interactively obtain additional information. For example, clicking on the etiology icon causes a display of information 760 within the Whiteboard 730, which includes a small interactive icon 762 displayed under the risk factors section (third bullet), whereby clicking on this interactive icon produces, for example, graphs pertaining to the genetics of the disease, displayed in a manner similar to that shown in FIG. 11.

In some embodiments, online tutorials and walkthroughs for new users may be made available. The content of the tutorials and walkthroughs may be based on the specific user type selected. For example, as shown in FIG. 7, for a selected user type of medical (physician), an image of a physician 740 is presented at the bottom left corner. Activation of this feature will cause a video tour and guidance of the site, the disease system page, the disease detailed page, etc., to be provided. This feature may also provide updates, as well as information on any new landmark clinical trials, changes in clinical guidelines, emerging pipeline agents, as well as any changes to the physician resources and key reference changes. In circumstances where another user type is selected, a corresponding representative image of such a user type may be displayed, and information about the site and/or any of the pages and available options relevant to the selected user type will be provided.

Figure 15:
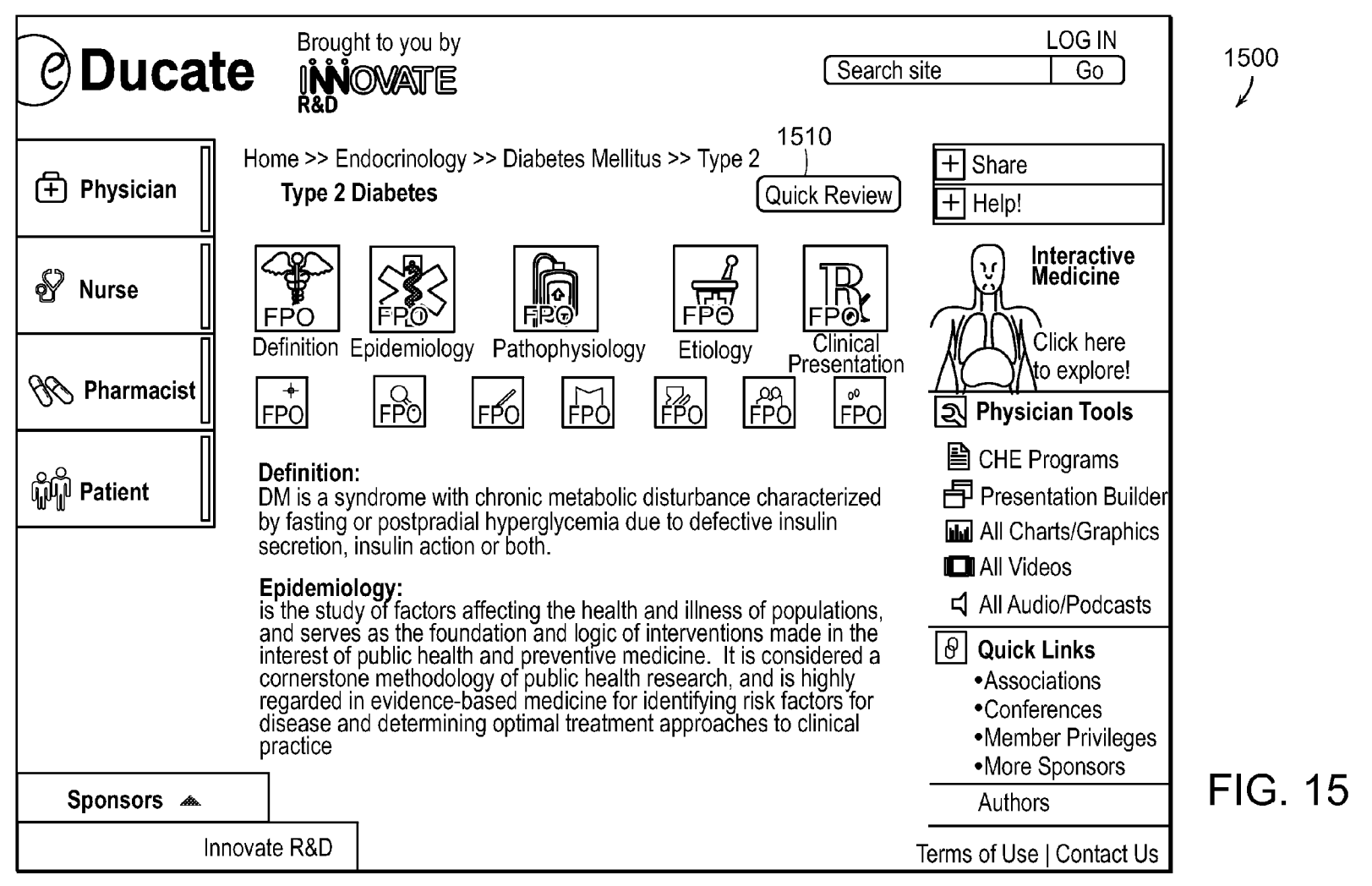

FIG. 15 is an image of another example detail page 1500, similar to the detail page 700 of FIG. 7, configured to also enable interaction by, and access to data for, practitioner type and/or a non-practitioner type. Selection of a practitioner user type will cause presentation of information common to all practitioner type (such information may be, in some embodiments, also available to the non-practitioner type users), and information that is specific to the selected practitioner type.

Similar to the disease detail page 700 of FIG. 7, the top row of selectable items (corresponding to Definition, Epidemiology, Pathophysiology, Etiology, and Clinical Presentation) may be common to all practitioner types, although, in some embodiments, the actual content presented in response to selection of those common selectable items may vary for different practitioner types.

The detail page 1500 may include, in some implementations, at least some of the features/tools of detail page 700. For example, in some embodiments, the detail page 1500 may include an interactive medicine tool, similar to the interactive model 1210 shown in FIG. 12, through which a user may explore and obtain information (graphical and text-based) regarding various physiological systems and conditions associated with them. The interactive medicine tool may be activated by clicking on it, or hovering over it. As noted, this tool may also be available from other pages/screens of the interface, including the pages depicted in FIGS. 4-6.

In some implementations, the detail page 1500 may include a Quick Review feature (activated by clicking, for example, on the selectable item 1510) to generate an executive summary of the item presented in the detail page. For example, in situations in which the interface 115 of the system 100 is used to present health care information, and the detail page may be used to present disease-specific information (customized and generated, based, at least in part, on the user type), the Quick Review feature causes the generation and presentation of an executive summary of the selected disease in table form. The Quick Review may generate an executive summary that is specific to a particular topic and pertinent to a particular user type, e.g., different practitioner types may be presented with different types of Quick Review executive summaries, whereas a non-practitioner user type may receive yet another executive summary suitable for that non-practitioner user type. The table-based executive summary may thus be based on the topic or sub-topic currently presented in the detail page, and on the particular user type reviewing that information. For example, FIG. 16 is table-formatted executive summary, generated, for example, by activating a Quick Review feature available from the detail page 1500, that provides an executive summary 1600 in relation to the topic of cluster headache. The executive summary 1600 was generated, in this example, for a physician user type, and provides the physician user type with relevant information regarding, for example, clinical presentation, differential diagnosis, investigation and workup, and treatment and guidelines. In some embodiments, the information for a certain topic may be provided only through the Quick Review feature and thus only in Quick Review format (i.e., executive summary in table-form). In some embodiments, where navigation to the detail pages (e.g., disease details) is performed, at least in part, through drill-down pages (such as the pages depicted in FIGS. 5 and 6), those drill down pages may include an indication (e.g., an icon or text data) that the detail page(s) accessible from the drill-down pages include, or are otherwise configured to provide, Quick Review type data. An example of such an indication to indicate to the user that Quick Review formatted data is accessible from a detail page is the symbol "QR."

Figure 17:
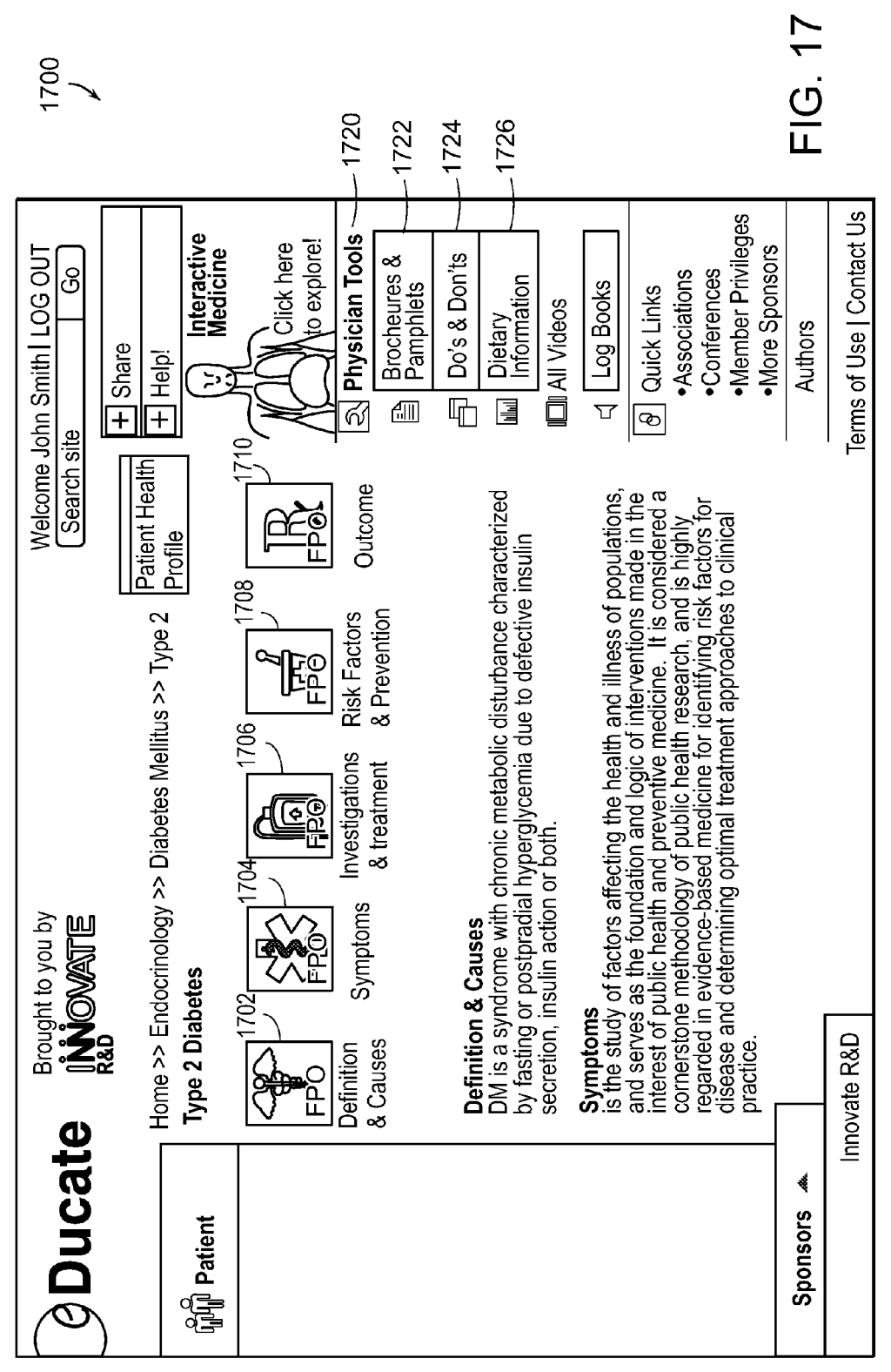

In some implementations, in response to selection of the selectable item associated with a non-practitioner user type, such as, for example, a patient, a non-practitioner-specific detail page (e.g., disease detail page) is invoked/presented. The non-practitioner type user may be directed to such a non-practitioner specific from a landing page (such as, for example, the landing pages depicted in FIGS. 3B and/or 14) or from a detail page such as the detail page 1500 shown in FIG. 15. With reference to FIG. 17, a patient-specific disease detail page 1700 is shown. In some implementations, the detail page 1700 may include selectable items (selected by clicking on the item, hovering over the item, etc.) to provide general information to the non-practitioner type user, without offering some of the selectable items that typically are available on the detail pages presented to practitioner type users. Thus, in some embodiments, the non-practitioner user type disease detail page may include (i) a Definition & Causes selectable item 1702, (ii) a Symptoms selectable item 1704, (iii) an Investigations & Treatment selectable item 1706, (iv) a Risk Factors & Prevention selectable item 1708, and (v) an Outcome selectable item 1710. Additional or fewer selectable items for different types/categories of information may be included. The non-practitioner detail page is generally configured to provide a brief lay-person overview of a disease.

In some embodiments, the five (5) components of the "tools" section 1720 (appearing on the right-hand-side of the page) may include tools for non-practitioner type users and thus be "non-practitioner-friendly" (e.g., "patient friendly"). The tools section 1720 may replace the CHE programs tool, presentation builder tool, and other tools that may be used in conjunction with information presentation for practitioner-type users (as shown, for example, in relation to FIGS. 7 and 15), with one or more of the following tools:

(1) Brochures/Pamphlets tool 1722 configured to provide the non-practitioner type user with, for example, additional information about diseases, medical condition, etc. (e.g., present pamphlets on diabetes or cholesterol);
(2) Do's & Don'ts tool 1724 configured to present information about, for example, healthy choices and compliance with medications;
(3) Diet tool 1726 configured to present information regarding dietary choices, including, for example, potential food interactions with medications;
(4) Log book tool 1728 configured to provide a downloadable outline for guidance to patients to track and monitor specific health issues, including but not restricted to, dietary changes, exercise, weight and blood pressure measurements, medication side effects, etc.; and
(5) Videos tool 1730 configured to present educational lay-person videos on specific disease areas.

Other types of non-practitioner-type tools may also be included and used.

In some embodiments, the Quick Review feature, available, for example, on practitioner-type interface pages (as in FIG. 15) may be replaced in a patient detail page with a "Patient Health Profile" feature that, when invoked, enables a patient to populate a standardized template regarding with information relating to his/her health and to upload supplemental information (e.g., tracking the physical signs and symptoms, for example, blood pressure, incidents of pain, laboratory reports etc.) An example of a Patient Health Profile 1800 is illustrated in FIG. 18. A Patient Health Profile can be printed by the patient or populated and left on the system, and may be password protected to safeguard the patient's privacy. The information included in a Patient Health Profile may be made available (e.g., at the patient's discretion) to the patient's caregivers. The patient may enable the sharing of the online Patient Health Profile information with their physicians, nurses and pharmacists by allowing password access to those practitioners. This may be particularly helpful if a patient forgets his/her their medications or records at home, and can simply log-in to his/her presentation system account to access the Health Profile information.

With reference again to FIG. 1, the information presentation management system 100 is configured, in some implementations, to track and bookmark, e.g., via digital cookies, users' use and navigation of the data presented on the interface. The system enables users to log in and return to the last place they viewed to enable seamless learning. The collection of browsing/viewing history information may be stored in local or remote storage (e.g., on a database formed and managed by the eDucate platform) and allows pharmaceutical, medical supply companies, etc., to access this users' use information and utilize this information to personalize their future marketing communications. In some embodiments, the system may be configured to generate e-mail communications transmitted at pre-determined time intervals (e.g., once a month) to users of the systems. The generated e-mail communications may be custom-personalized to the users based on, for example, the type of information accessed by respective users (as recorded, for example, in the database used to track users' use of the system 100). Such personalized e-mails may include such information as key news articles in the professional field of the users, conferences and cutting edge innovations, etc. The tracking/monitoring functionality of the system to track users' use of the system will also aid in the computer based training functionality that may be embedded in the system to track content reviewed for certification courses.

In some embodiments, the enhanced learning experience can be achieved by incorporating into the system 100 a built-in quizzing component to enable the user to turn the interactive session into a question and answer session for knowledge testing.

In some implementations, the system may be configured to present exams/tests to users. Specifically, the system may include a series of tiered examinations set to challenge individuals (e.g., medical, nursing and/or pharmacy students) at the beginner level, intermediate level (for those already graduated but enrolled in specialty programs), and advanced (at the level of the specialist). The format and configuration of the examinations may be such that both a pre- and post-test quizzes are administered, as well as formal style examinations modeled on the style of accrediting organizations (e.g., accrediting medical bodies). Users may be able to select the style of examination desired.

Additionally, users may, in some embodiments, use a tool to track and display the courses, quizzes and examinations the users have enrolled in and completed, as well as the level of completion of the courses and successes on various teats, quizzes and examinations. That information may be stored and processed to provide users with a measure of their progress relative to other users whose performance is being tracked and stored. Similarly, for accredited CHE programs, users will be able to keep a record/print or of the courses successfully completed and be able to use this to support their re-accreditation as may be required by governing bodies. In some embodiments, the tracking tool may be implemented as a 'gas-meter' to help the user understand their level of success as compared to peers and/or amount of accredited CHE courses successfully completed. That is, the user is provided with a graphical representation, such as a vertical bar or a gauge with a dial, of the user's progress through the site quizzes. The gas meter tool can provide a straight percentage score and/or a percentile score among their peers. For example, if a user has received a 50% score, the score may be presented as a ½ empty gas tank. In some variations, incentives to entice users to successfully complete accredited CHE programs or board examination preparation tests may be provided by, for example, offering users sponsorship/grants to attend various conferences. As part of the exam preparation process, the system may enable establishing on-line study and review groups and meeting rooms (akin to chat rooms) within the interface to encourage knowledge transfer and learning. Establishing on-line study and review groups may also include, in some embodiments, in-class room, in-lab and in-operating room web feeds with possible interactive capabilities such as an 'Ask the Professor' feature. An important objective would be to establish an association with governing bodies that would allow CHE credits earned from completion of accredited CHE programs to be electronically sent/reported directly to the governing body. As well, with appropriate security measures, including the performance of authentication and data encryption procedures, the interface/portal may be used to conduct formal accredited examinations. The database of data relating to the one or more subject matters (including text-based data, pictures, images, and videos) could be used as a data repository for health organizations and accrediting organizations to store accredited examination to be administered to users.

Another feature of the interface/portal described herein is the configuration of a sub-portal to implement and facilitate e-commerce. Accessing of this sub-portal enables a user to select an area of interest, for example, medicine. Within the sub-portal the user may receive information relating to medical tools and devices, including such personal devices/tools as stethoscopes, blood pressure cuffs, computers, etc., to more specialized equipment such as catheters, syringes, etc. The e-commerce sub-portal may also be configured to support e-commerce in relation to products for other technologies and fields. For example, the same or a different sub-portal may be dedicated to facilitating e-commerce for natural science fields (chemistry, physics, etc.) Suppliers of various chemicals and laboratory equipment would thus be able to present their products to users of the information presentation management system, which may then be purchased via the sub-portal. An advantage of this particular approach is that multiple companies can access and transact on a single platform (e.g., the platform implemented by the information presentation management system), while at the same time making it advantageous for consumers to perform comparison shopping rather than searching specific websites of many different companies. In addition, the sub-portal could provide information regarding event tickets, airline tickets, rental cars, books and other merchandise marketed by sponsors of the system 100. Similar to on-line study groups described herein, an e-commerce board to facilitate commercial trading, including book and equipment exchanges, may be established within this sub-portal.

As described herein, the system (e.g., the eDucate platform) is configured to distill large bodies of information to present data in a clear and concise fashion and in a standardized manner to facilitate learning. The system can be adapted to present and manage information for different professional and non-professional areas to provide users with access to information (e.g., stored on one or more local and/or remote data repositories). When adapted to present and manage information pertaining to non-medical subject matters/fields, the system's landing page may be implemented so as to accommodate various entrance portals, for example dentistry, natural sciences (biochemistry, physics, biology, etc.), sociology, languages, etc. Thus, when adapted to present and manage information (including educational information) for dentistry, for example, a drill-sown interface, similar to the drill-down interface described in relation to health care subject matters and depicted in FIGS. 3-12, may be implemented. Accordingly, when drilled down to a specific disease page in relation to dental health, similar to the disease-specific page 700 of FIG. 7, the interface may include dentist specific user selectable items (e.g., selectable icons) corresponding to such information and tools for a clinical presentation tool, treatment and guidelines, etc., which can be formatted and used to promote clear standardized access to dental information. A disease page that includes interactive anatomy and sponsors information will all remain fairly consistent with respect to the disease page used for the medical subject matter shown in FIG. 7. Such a page may thus also include user-selectable items to access information and tools common to two or more user types (which for the dental profession may include, for example, a dentist, s dental assistant, a dental hygienist, etc.), including such tools as a definition tool, an epidemiology tool, a pathophysiology tool, an etiology tool, etc.

For other fields, disciplines and/or subject matters, e.g., natural sciences, social sciences, arts, engineering, etc., the interface entrance page can be configured to reflect the one or more subject matters of interest, as well as some user-types having an interest in the information for that one or more subject matters. Using the natural sciences subject matter as an example, the entrance page (e.g., landing page) may have a similar appearance to the medical entrance page but may further include entrance "buttons" for chemistry, physics, biology, etc. Clicking on any one of these areas will drill through to a different sub-landing page. For example, clicking on chemistry will drill through to a page of main topics that would cover all pertinent areas of chemistry, e.g., atoms and atomic structure, periodic table, properties of gasses, solids and liquids, chemical bonding and molecular structure, chemical energetics, etc. A similar arrangement can be made for any topic in the natural sciences. In some embodiments, selection of the particular subject matter may lead to a subsequent page in which a plurality of user types relevant to the selected subject matter are presented, and upon selection of the user type, the system presents and manages the information based on the selected subject matter and the selected user-type. In some embodiments, selection of the user type is performed from the same page where the subject matter is selected.

Furthermore, the information presentation management system described herein may be applied to virtually all aspects of learning at all levels from university to kindergarten level. At elementary levels interactive icons can be simplified to teach phonics, basic English, mathematics, and simple introductory language and social skills. Online learning will leverage cutting edge technology such as in-class room, in-lab and in-operating room live web feeds with interactive capabilities such as an 'Ask the Professor' feature and digital whiteboard technology. Community forums for universities, hospitals students, etc., may be developed to assist students in finding, for example, available schools, employment and rotation placements, preparatory courses and lodging.

Additionally, the e-learning functionality of the information presentation management system described herein may be configured and used to display topics within any learning area at any educational level, and may be presented/translated into many languages. Through use of the system described herein, a complex subject matter may be presented in a simplified manner to the lay public. For example, people suffering from serious medical conditions/illnesses would benefit from receiving further information regarding cause(s) of their conditions, treatment thereof, and expected outcomes in an easy to understand format. The information presentation management system described herein may, in some embodiments, be configured to provide a sub-landing page listing many different diseases and to enable a user to drill through to the appropriate disease conditions to provide basic lay-person information on the diseases, treatments (including medications) and management thereof, as well as simple illustrations and videos on the medical condition and the potential benefits of the corresponding treatment. Furthermore, podcasts can be used by various medical agencies and pharmaceutical companies to provide a wide range of lay public medical information such as the signs and symptoms of any disease, e.g., stroke or heart attack. A general public presentation system may have a similar appearance to the interfaces used to present information to professional practitioner, but may have simplified icons that would read, for example, in relation to diabetes, as follows: "What is diabetes", "How do you get diabetes", "How many people may have diabetes", "What can you do when you get diabetes", "What should you tell your doctor", "Drugs that may be given to you by your doctor", "Common side effects of some of these drugs", "dietary restrictions and considerations", "Healthy lifestyle and eating", "Importance of exercise", "Resources", "References", etc. These topics may be set out in a standardized set of, for example, icons to display information on the "whiteboard" with simplified interactive components as set out for the more in-depth medical learning intended for professional user types. Such a system for the lay public, which may be accessible through a network, may also contain information from sponsors about their products and information from local, regional, provincial, national, and international organizations (for example, the Juvenile Diabetes Foundation) regarding the disease or regarding any relevant subject matter with respect to which information is being provided to the public.

The subject matter described herein can be implemented as one or more computer program products, i.e., one or more computer programs tangibly embodied in a machine-readable storage device, for execution by, or to control the operation of, data processing apparatus, e.g., a programmable processor, a computer, or multiple computers.

A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program, or in multiple coordinated files (e.g., files that store one or more modules, sub-programs, or portions of code). A computer program can be deployed to be executed on one computer or on multiple computers at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both.

The computing system can include clients and servers. A client and server are generally remote from each other in a logical sense and typically interact through a communication network. The relationship of client and server arises by virtue of computer programs running on the respective computers and having a client-server relationship to each other.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method for managing presentation of information, the method performed by execution of computer readable program code by a processor of a computer system, the method comprising:
retrieving information relating to one or more subject matters from one or more data repositories, the one or more subject matters including general non-personal information on medical conditions and treatments therefor;
presenting one or more sets of data from the retrieved information specific to a practitioner type selectable by a user from a plurality of practitioner types;
presenting another one or more sets of data from the retrieved information common to two or more practitioner types selectable from the plurality of practitioner types;
presenting a further one or more sets of data from the retrieved information specific to at least one non-practitioner type;
presenting an anatomical model comprising a plurality of model layers; and
presenting, in response to selection of one of the plurality of model layers and selection of a position within the selected one of the plurality of model layers, medical data based on the selected position and the selected one of the plurality of model layers, and further based on a user type selected from the plurality of practitioner types and the non-practitioner type, the medical data comprising one or more of diseases relating to the selected position and the selected one of the plurality of model layers, or pharmaceutical drugs relating to the selected position and the selected one of the plurality of model layers;
wherein at least one screen, for presenting at least some of the retrieved information on an interface, includes in one area of the at least one screen data from the one or more sets of data specific to a selected practitioner type, and includes on another area of the at least one screen other data from the retrieved information common to the selected practitioner type, and at least one other of the plurality of practitioner types;
and wherein the at least one screen includes a disease detail page with information relating to a selected disease, the disease detail page including:
a first area including user selectable items common to the selected practitioner type, and the at least one other of the plurality of practitioner types, the user selectable items of the first area including at least one or more of a disease definition icon, an epidemiology icon, a pathophysiology icon, an etiology icon, or a clinical presentation icon;
a second area including selectable items specific to the selected practitioner type that change depending on the selected practitioner type; and
a third area including data relating to the selected disease retrieved in response to selection of one of the user selectable items from the first area or the second area.

2. The method of claim 1, wherein the one or more subject matters include health care.

3. The method of claim 1, wherein the plurality of practitioner types includes one or more of: a physician, a nurse, a pharmacists, a physician assistant, a doctor of osteopathy, a paramedic/emergency medical technician (EMS), a registered practical nurse, a nursing aide and a health care student, and wherein the at least one non-practitioner type includes a patient.

4. The method of claim 2, wherein presenting the other one or more sets of data common to the two or more practitioner types comprises:
displaying on a display device a landing page identifying at least one of the two or more practitioner types, the at least one non-practitioner type, and the one or more subject matters, the landing page including user selectable items respectively associated with the at least one of the two or more practitioner types and the at least one non-practitioner type.

5. The method of claim 2, further comprising:
presenting on the landing page, in response to selection of one of the user selectable items identifying the at least one of the two or more practitioner types, a menu including a listing of topics relating to the one or more subject matters; and
presenting, when a selectable topic from the listing of topics is associated with one or more drill-down levels of sub-menus of sub-topics relating to the selectable topic, one of the one or more drill-down levels in response to selection of an item from a sub-menu of a preceding drill-down level associated with the selectable topic and with the one of the one or more drill-down levels of sub-menus.

6. The method of claim 5, wherein the listing of topics includes a listing of health care topics, and wherein the one of the one or more drill-down sub-menus includes a list of diseases associated with the selected topic.

7. The method of claim 6, further comprising: presenting, in response to selection of the disease from the list of diseases associated with the selected topic, the disease detail page containing data specific to the selected disease.

8. The method of claim 7, wherein presenting the disease detail page comprises:
when the at least one non-practitioner type is selected, presenting a disease definition and causes icon, a symptom icon, an investigation and treatment icon, a risk factor and prevention icon, and an outcome icon.

9. The method of claim 1, further comprising:
displaying, in response to selection of one of the user selectable items identifying the at least one of the two or more practitioner types, a topics page including a listing of topics relating to the one or more subject matters.

10. The method of claim 1, further comprising:
presenting a tools menu identifying one or more computer-implemented tools to perform one or more of accessing available data and processing the available data.

11. The method of claim 10, wherein, when the practitioner type is selected, the one or more computer-implemented tools comprise: a Continuing Health Education tool implemented for a topic selected from a listing of topics presented in a topics page to present to the user educational materials relating to the selected topic; a Presentation Builder tool to construct a presentation based on one or more of an audio data and visual data to be provided to the user; an All Video tool to present videos relating to the topic selected from the listing of topics presented in the topics page; an Audio and Podcast tool to present audio data relating to the topic selected from the listing of topics presented in the topics page; and a Charts and Graphs tool to present graphical information relating to the topic selected from the listing of topics presented in the topics page.

12. The method of claim 10, wherein, when the non-practitioner type is selected, the one or more computer-implemented tools comprise: a Brochures/Pamphlets tool configured to provide the non-practitioner type user with additional information about a selected disease; a Do's & Don'ts tool configured to present information about healthy choices and compliance with medications; a Diet tool configured to present information regarding dietary choices; a Log book tool configured to provide a downloadable outline for guidance to patients to track and monitor specific health issues, the health issues including one or more of: dietary changes, exercise, weight and blood pressure measurements, and medication side effects; and a Videos tool configured to present educational videos on specific disease areas.

13. The method of claim 1, further comprising:
presenting, when the practitioner type is selected, a quick review selectable item that, when selected, causes the presentation of an executive summary of one or more selected diseases in table format.

14. The method of claim 1, further comprising:
presenting, when the non-practitioner type is selected, a patient health profile selectable item that, when selected, enables performing one or more of: recording and maintaining user-specific health information, and recording and maintaining user non-specific supplemental health information.

15. A system to manage presentation of information, the system comprising:
an audio-visual display device to present data;
a processor-based computing device; and
a storage device to store computer instructions that, when executed on the processor-based computing device, cause the processor-based computing device to:
retrieve information relating to one or more subject matters from one or more data repositories, the one or more subject matters including general non-personal information on medical conditions and treatments therefor;
present one or more sets of data from the retrieved information specific to a practitioner type selectable by a user from a plurality of practitioner types;
present another one or more sets of data from the retrieved information common to two or more practitioner types selectable from the plurality of practitioner types;
present a further one or more sets of data from the retrieved information specific to at least one non-practitioner type;
present an anatomical model comprising a plurality of model layers; and
present, in response to selection of one of the plurality of model layers and selection of a position within the selected one of the plurality of model layers, medical data based on the selected position and the selected one of the plurality of model layers, and further based on a user type selected from the plurality of practitioner types and the non-practitioner type, the medical data comprising one or more of diseases relating to the selected position and the selected one of the plurality of model layers, or pharmaceutical drugs relating to the selected position and the selected one of the plurality of model layers;
wherein at least one screen, for presenting at least some of the retrieved information on an interface, includes in one area of the at least one screen data from the one or more sets of data specific to a selected practitioner type, and includes on another area of the at least one screen other data from the retrieved information common to the selected practitioner type, and at least one other of the plurality of practitioner types;
and wherein the at least one screen includes a disease detail page with information relating to a selected disease, the disease detail page including:
a first area including user selectable items common to the selected practitioner type, and the at least one other of the plurality of practitioner types, the user selectable items of the first area including at least one or more of a disease definition icon, an epidemiology icon, a pathophysiology icon, an etiology icon, or a clinical presentation icon;
a second area including selectable items specific to the selected practitioner type that change depending on the selected practitioner type; and
a third area including data relating to the selected disease retrieved in response to selection of one of the user selectable items from the first area or the second area.

16. The system of claim 15, wherein the computer instructions further comprise instructions that, when executed on the processor-based computing device, further cause the processor-based computing device to:
present, when the practitioner type is selected, a quick review selectable item that, when selected, causes the presentation of an executive summary of one or more selected diseases in table format; and
present, when the non-practitioner type is selected, a patient health profile selectable item that, when selected, enables performing one or more of: recording and maintaining user-specific health information, and recording and maintaining user non-specific supplemental health information.

17. A non-transitory computer program product residing on a computer readable storage device and comprising computer instructions that, when executed on at least one processor-based device, cause the at least one processor-based device to:
retrieve information relating to one or more subject matters from one or more data repositories, the one or more subject matters including general non-personal information on medical conditions and treatments therefor;
present one or more sets of data from the retrieved information specific to a practitioner type selectable by a user from a plurality of practitioner types;
present another one or more sets of data from the retrieved information common to two or more practitioner types selectable from the plurality of practitioner types;
present a further one or more sets of data from the retrieved information specific to at least one non-practitioner type;
present an anatomical model comprising a plurality of model layers; and
present, in response to selection of one of the plurality of model layers and selection of a position within the selected one of the plurality of model layers, medical data based on the selected position and the selected one of the plurality of model layers, and further based on a user type selected from the plurality of practitioner types and the non-practitioner type, the medical data comprising one or more of diseases relating to the selected position and the selected one of the plurality of model layers, or pharmaceutical drugs relating to the selected position and the selected one of the plurality of model layers;
wherein at least one screen, for presenting at least some of the retrieved information on an interface, includes in one area of the at least one screen data from the one or more sets of data specific to a selected practitioner type, and includes on another area of the at least one screen other data from the retrieved information common to the selected practitioner type, and at least one other of the plurality of practitioner types;

and wherein the at least one screen includes a disease detail page with information relating to a selected disease, the disease detail page including:
- a first area including user selectable items common to the selected practitioner type, and the at least one other of the plurality of practitioner types, the user selectable items of the first area including at least one or more of a disease definition icon, an epidemiology icon, a pathophysiology icon, an etiology icon, or a clinical presentation icon;
- a second area including selectable items specific to the selected practitioner type that change depending on the selected practitioner type; and
- a third area including data relating to the selected disease retrieved in response to selection of one of the user selectable items from the first area or the second area.

18. The method of claim 1, further comprising:
presenting a cellular layer of the anatomical model, the cellular layer including cell data representative of different cells of a human body; and presenting, in response to selection of a position within the cellular layer, other layer data, corresponding to the selected position within the cellular layer, from other layer data corresponding to another of the plurality of layers.

19. The method of claim 1, further comprising:
presenting at least a portion of the anatomical model data selected from a plurality of model data sets that each corresponds to a different one of the plurality of practitioner types and the at least one non-practitioner type, each of the plurality of model data sets comprising a respective plurality model layers, wherein each of the respective plurality of layers is representative of a respective anatomical system.

20. The method of claim 1, wherein when one or more positions are selected on the interactive anatomical model medical data corresponding to the selected one or more positions is displayed including data corresponding to the one or more positions in the anatomical model that is specific to the selected user type and additional data corresponding to the one or more positions in the anatomical model common to the selected user type and at least one other of the plurality of user types.

* * * * *